(12) United States Patent
Wan et al.

(10) Patent No.: US 9,101,615 B2
(45) Date of Patent: Aug. 11, 2015

(54) INTRAVENOUS FORMULATIONS OF NEUROKININ-1 ANTAGONISTS

(75) Inventors: Jiansheng Wan, Warren, NJ (US);
Pranav Gupta, Short Hills, NJ (US);
David Monteith, Pittstown, NJ (US);
Soumendu Bhattacharya, East Windsor, NJ (US)

(73) Assignee: OPKO Health, Inc., Miami, FL (US)

( * ) Notice: Subject to any disclaimer, the term of this patent is extended or adjusted under 35 U.S.C. 154(b) by 701 days.

(21) Appl. No.: 12/855,889

(22) Filed: Aug. 13, 2010

(65) Prior Publication Data
US 2011/0038925 A1 Feb. 17, 2011

Related U.S. Application Data

(60) Provisional application No. 61/234,129, filed on Aug. 14, 2009.

(51) Int. Cl.
| | |
|---|---|
| A61K 9/48 | (2006.01) |
| A61K 31/44 | (2006.01) |
| A61K 9/00 | (2006.01) |
| A61K 9/107 | (2006.01) |
| A61K 47/14 | (2006.01) |
| A61K 47/24 | (2006.01) |
| A61K 47/44 | (2006.01) |

(52) U.S. Cl.
CPC ............... *A61K 31/44* (2013.01); *A61K 9/0019* (2013.01); *A61K 9/1075* (2013.01); *A61K 47/14* (2013.01); *A61K 47/24* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,610,140 A * | 3/1997 | Goodfellow et al. ........ 514/12.2 |
| 5,620,989 A | 4/1997 | Harrison et al. |
| 5,661,162 A | 8/1997 | MacLeod et al. |
| 5,760,018 A | 6/1998 | Baker et al. |
| 6,162,805 A | 12/2000 | Hefti |
| 6,329,394 B1 * | 12/2001 | Hagan et al. ................... 514/329 |
| 6,329,401 B1 | 12/2001 | Mendel et al. |
| 6,436,928 B1 | 8/2002 | Shih et al. |
| 6,499,984 B1 | 12/2002 | Ghebre-Sellassie et al. |
| 6,635,639 B2 | 10/2003 | Arora et al. |
| 7,041,682 B2 | 5/2006 | Shih et al. |
| 7,049,320 B2 * | 5/2006 | Paliwal et al. ................. 514/278 |
| 7,122,677 B2 | 10/2006 | Reichard et al. |
| 7,183,272 B2 | 2/2007 | Aronhime et al. |
| 7,323,459 B2 | 1/2008 | Dolitzky et al. |
| 7,534,913 B2 | 5/2009 | Frenkel et al. |
| 7,563,801 B2 | 7/2009 | Qiu et al. |
| 7,709,641 B2 | 5/2010 | Shah et al. |
| 7,879,867 B2 | 2/2011 | Paredes et al. |
| 7,897,613 B2 | 3/2011 | Arul et al. |
| 7,902,366 B2 | 3/2011 | Paliwal et al. |
| 7,981,905 B2 | 7/2011 | Qiu et al. |
| 8,178,550 B2 | 5/2012 | Hu et al. |
| 8,273,895 B2 | 9/2012 | Paliwal et al. |
| 8,470,842 B2 | 6/2013 | Hu et al. |
| 2001/0007663 A1 | 7/2001 | Von Corswant |
| 2003/0158173 A1 | 8/2003 | Paliwal et al. |
| 2005/0131011 A1 | 6/2005 | Stupple |
| 2005/0153999 A1 * | 7/2005 | Hu ................................. 514/278 |
| 2006/0094720 A1 | 5/2006 | Shih et al. |
| 2006/0223804 A1 | 10/2006 | Shah et al. |
| 2007/0207201 A1 * | 9/2007 | Krishnan et al. .............. 424/455 |
| 2009/0048346 A1 * | 2/2009 | Zentner et al. ................. 514/622 |
| 2010/0087426 A1 | 4/2010 | Mergelsberg et al. |

(Continued)

FOREIGN PATENT DOCUMENTS

| | | |
|---|---|---|
| EP | 0790248 A1 | 8/1997 |
| EP | 1970050 A1 | 9/2008 |

(Continued)

OTHER PUBLICATIONS

International Journal of Pharmaceutics 348 (2008) 70-79, A lipid microsphere vehicle for vinorelbine: Stability, safety and pharmacokinetics by Zhang et al.*

(Continued)

*Primary Examiner* — Snigdha Maewall
(74) *Attorney, Agent, or Firm* — Choate, Hall & Stewart LLP; Brenda Herschbach Jarrell; Kristen C. Buteau

(57) ABSTRACT

Pharmaceutical compositions for intravenous administration comprising the compound of Formula I Formula I

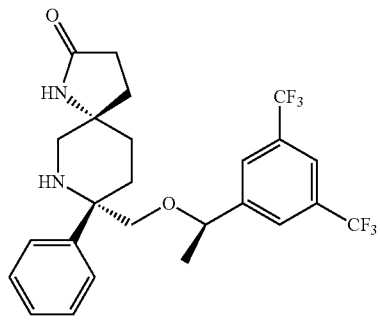

or pharmaceutically acceptable salts, hydrates or prodrugs thereof are described herein. Methods of preparing the pharmaceutical compositions and methods for treating nausea and/or emesis with the pharmaceutical compositions are also described herein.

44 Claims, 13 Drawing Sheets

(56) References Cited

U.S. PATENT DOCUMENTS

| | | |
|---|---|---|
| 2010/0104637 A1 | 4/2010 | Qiu et al. |
| 2011/0038925 A1 | 2/2011 | Wan et al. |
| 2011/0098468 A1 | 4/2011 | Paliwal et al. |
| 2012/0015921 A1 | 1/2012 | Qiu et al. |
| 2013/0023503 A1 | 1/2013 | Paliwal et al. |
| 2013/0122088 A1 | 5/2013 | Qiu et al. |
| 2013/0281477 A1 | 10/2013 | Hu et al. |
| 2014/0088128 A1 | 3/2014 | Qiu et al. |
| 2014/0336158 A1 | 11/2014 | Paliwal et al. |

FOREIGN PATENT DOCUMENTS

| | | | |
|---|---|---|---|
| WO | 94/10165 A1 | 5/1994 | |
| WO | 94/13639 A1 | 6/1994 | |
| WO | 95/19344 A1 | 7/1995 | |
| WO | 96/26726 A1 | 9/1996 | |
| WO | WO-00/71163 A1 | 11/2000 | |
| WO | 01/44200 A2 | 6/2001 | |
| WO | 03/042173 A1 | 5/2003 | |
| WO | 03/051840 A1 | 6/2003 | |
| WO | WO-03/051840 A1 | 6/2003 | |
| WO | WO-2004/082676 A1 | 9/2004 | |
| WO | 2005/063243 A1 | 7/2005 | |
| WO | WO-2006/017246 A2 | 2/2006 | |
| WO | WO-2007/117486 A2 | 10/2007 | |
| WO | WO-2007-114921 A1 | 11/2007 | |
| WO | WO-2008-118331 A1 | 10/2008 | |
| WO | WO-2010/028232 A1 | 3/2010 | |

OTHER PUBLICATIONS

Cogan, et al., "Tetrahedron". 55 (1999), 8883-8904.
Giard, et al., "Tetrahedron Letters", 40 (1999), 5495-5497.
Gonzalez, et al., "Oncology Special Edition, 5"; (2001), 53-58.
Grote, et al., :Combination Therapy for Chemotherapy-Induced Nausea and Vomiting in Patients Receiving Moderately Emetogenic Chemotherapy: Palonosetron, Dexamethasone, and Aprepitant. J Support Oncol, Sep. 2006, vol. 4, No. 8:403-408.
Harrison, T., et al., "Gem-Disubstituted Amino-Ether Based Substance P Antagonists", Bioorganic & Medicinal Chemistry Letters. vol. 4, No. 23; 1994; pp. 2733-2734.
International Search Report corresponding to PCT/US2005/023427 dated Jan. 26, 2006.
International Search Report corresponding to PCT/US2007/008345 dated Jan. 22, 2008, 4 pages.
International Search Report corresponding to PCT/US2010/045317 dated Oct. 14, 2010.
Kramer,et al. "Science, 281"; (1998), 1640-1645.
Kubik, et al. "Tetradron Letters, 35"; (1994), 6635-6638.
Miaskkowski, et al., "Cancer Pain"; Nov. 2005.
Noory, et al., "Steps for Development of a Dissolution Test for Sparingly Water Soluble Drug Products, Dissolution Technologies", Feb. 2000, Article 3.
O'Donnell, et al. "Heterocycles, 46", (1997), 617-630.
Pendergrass, et al., "Aprepitant; An Oral NK1 Antagonist for the Prevention of Nausea and Vomiting Induced by Highly Emetogenic Chemotherapy". Drugs Today (Barc). 2004, vol. 40(10): 853-863; abstract only.
Reddy, et al., "Novel Neurokinin-1 Antagonist as Antiemetics for the Treatment of Chemotherapy-Induced Emesis, Supportive Cancer Therapy", Apr. 1, 2006; 3(3); 140-2.
Rogiers, et al., "Stereoselective Conversation of 2H-1, 4-Oxazin-2-Ones Into 2,5,5-Substituted Piperidine-2-Carboxamides and 2-Methanamines and Related Octahydro-2H-Pyrido[1,2-a]pyrazines, Potential Substance P Antagonists", Tetrahendron, vol. 57: 2001; 8971-8981.
Rogiers, et al. Tetrahedron (2003), 59(27), 5047-5054.
Rombouts, et al., "Synthesis and Conformational Analysis of Substance P Antagonist Analogues Based on a 1,7-naphthyradine Scaffold", Tetrahedron, vol. 59; 2003; 4721-4731.
Rombouts, et al. Tetrahedron Letters, 42; (2001), 7397-7399.
Wu, X., et al., "Generation of Cyclopenta[c]piperidines and Pyrrolo[3,4-c]pipidines-Potential Substance P Antagonists-from Adducts of Cyclic Dienophiles and 5-chloro-6-Methyl-3-Phenly-2H-1,4-Oxazin-2-one", Tetrahendron, vol. 56; 2000; 6279-6290.
Wu, X., et al., "Stereoselective Transformation of 2H-1, 4 Oxazin-2-ones into 2, (2), 5, 5-Tri-and Tetrasubmitted Analogues of cis-5-Hydroxy-2-piperidinemethanol and cis-5-Hydroxy-6-oxo-2-piperidinecarboxylic Acid", Tetrahedron, vol. 56; 2000; pp. 3043-3051.
Zhang, et al., "A Lipid Microsphere Vehicle for Vinarelbine: Stability, Safety and Pharmacokinetics". International Journal of Pharmaceutics, 2008, vol. 348, pp. 70-79, esp. p. 71-73.
International Preliminary Report on Patentability for PCT/US10/45317 (Publication No. WO 2011/019911) mailed Feb. 14, 2012.
Berge, S.M. et al., Pharmaceutical Salts, Review Article, Journal of Pharmaceutical Sciences (1997).
Brittain et al. Polymorphism in Pharmaceutical Dosage Forms, Polymorphism in Pharmaceutical Solids XX, 235-238 (1999).
Brittain et al. Polymorphism in Pharmaceutical Dosage Forms, Polymorphism in Pharmaceutical Solids XX, 348-361, see p. 357, second full paragraph (1999).
Brittain, Methods for the Characterization of Polymorphs and Solvates, Polymorphism in Pharmaceutical Solids, 95(6):227-278 (1999).
Brittain, Spectral Methods for the Characterization of Polymorphs and Solvates, Journal of Pharmaceutical Sciences, 86(4) (1997).
Database Prousddr, Prous Science, Provenza, 388, 1 page (May 9, 2004).
Duffy, R.A., Potential therapeutic targets for neurokinin-1 receptor antagonists, Expert Opinion on Emerging Drugs, 9(1):9-21 (2004).
Geselbracht, M., Reed College, Introduction to X-ray Powder Diffraction, posted on VIPEr on Feb. 22, 2008.
Giard, T. et al., Pyrrolidines bearing a quaternary a-stereogenic center. Part 1: Synthesis of analogs of ABT-418, a powerful nicotinic agonist, Tetrahedron Letters, 40:5495-5497 (1999).
International Search Report for PCT/US02/40203, 4 pages (Apr. 24, 2003).
International Search Report, PCT/US2007/008344, 6 pages (Oct. 25, 2007).
Knabe, J. et al., Racemates and Enantiomers of Basic Substituted 5-Phenylhydantoins, Pharmazie, 52(12):912-919 (1997).
Morissette, S.L. et al., High-throughput crystallization: polymorphs, salts, co-crystals and solvates of pharmaceutical solids, Advanced Drug Delivery Reviews, 56:275-300 (2004).
Oh, C. H. et al., Synthesis of New Hydantoin-3-Acetic Acid Derivatives, Bulletin of the Korean Chemical Society, 9(4):231-235 (1988).
Otsuka et al., Comparative Determination of Polymorphs of Indomethacin in Powders and Tablets by Chemometrical Near-Infrared Spectroscopy and X-ray Powder Diffractometry, AAPS PharmSciTech, 4(2), Article 19:1-12(2003).
Sarna, S.K. and Otterson, M.F., Small intestinal physiology and pathophysiology, Gastroenterology Clinics of North America, 18(2):375-404 (1989). (abstract).
Schulte, K.E. et al., Hydantoin-Derivate as Potential Anti-inflammatory Substances, European Journal of Medical Chemistry-Chimica Therapeutica, 13(1):25-31 (1978).
Vippagunta, S.R. et al., Crystalline solids, Advanced Drug Delivery Reviews, 48:3-26 (2001).
European Search Report of EP 10808756.0, 6 pages (Nov. 12, 2012).
Diemunsch et al., Neurokinin-1 Receptor Antagonist in the Prevention of Postoperative Nausea and Vomiting, British Journal of Anaesthesia, 103(1): 7-13 (2009).
Written Opinion for PCT/US2010/045317, 10 pages (mailed Oct. 14, 2010).
U.S. Appl. No. 14/540,635, filed Nov. 13, 2014, Qiu et al.

* cited by examiner

Schematic Representation of the Method for Manufacture NK-1 Emulsion Formulations

BOL10WSO

1 pass H30Z 5000 psi 3 passes H30Z 5000 psi 1 pass H30Z 2000 psi 3 passes H30Z 2000 psi

INTRAVENOUS FORMULATIONS OF NEUROKININ-1 ANTAGONISTS

FIELD OF THE INVENTION

The present invention relates to pharmaceutical compositions of a neurokinin-1 antagonist and pro-drugs thereof for intravenous administration, production of the pharmaceutical compositions and their use.

BACKGROUND OF THE INVENTION (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I; also referred herein as Compound 1) and salts thereof have been described in U.S. Pat. No. 7,049,320 (the '320 patent), issued May 23, 2006. A process for the synthesis of Compound 1 is specifically exemplified in Example 72a of the '320 patent (See the '320 patent at col. 43, line 55 to col. 45, line 20; col. 75, line 55 to col. 80, line 21; col. 90 lines 35 to 63; and col. 98, line 1 to col. 99, line 24, which is herein incorporated by reference. See also WO2008/11833, Examples 1-6, which are herein incorporated by reference). WO 2005/063243 discloses certain pharmaceutical compositions comprising NK-1 antagonists. The formulations described therein require a polyanionic beta-cyclodextrin derivative with about one to seven sodium sulfonate groups separated from the lipophilic cavity by at least one butyl ether spacer group—i.e., Captisol®. There is no reference therein to iv formulations which minimize hemolysis. In addition, various salt forms of a compound of Formula I have been described in, for example, U.S. Pat. Publication 2007/0244142 and which is also incorporated by reference.

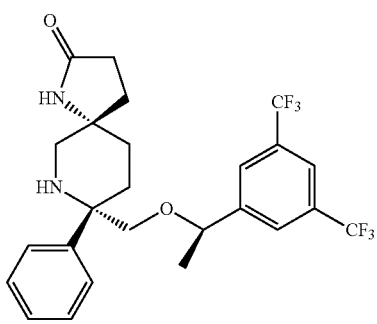 [SMILES: C[C@@H](OC[C@@]1(c2ccccc2)CC[C@]2(CCC(=O)N2)CN1)c1cc(C(F)(F)F)cc(C(F)(F)F)c1]

Formula I

The compound of formula I is classified as a tachykinin compound and is an antagonist of neuropeptide neurokinin-1 (NK-1) receptors. The compound of formula I may be in the form of a free base or in the form of a pharmaceutically acceptable salt. The free base or salt may be in the amorphous form or the pharmaceutically acceptable salt used herein may be in a crystalline form or crystalline hydrate or solvate form. In solution and depending upon the pH of such solution, the compound of formula I may be in the form of a mixed free amine/salt form. Prodrugs of a compound of formula I may also be utilized in the formulations suitable for parenteral administration. Prodrugs wherein either free amine (or both amines) in a compound of formula I has the hydrogen replaced with a group selected from —Y and salts thereof wherein Y is selected from —P(O)(OH)$_2$, —S(O)$_{n1}$R$^1$, —C(O)(C$_{1-6}$alkyl)X, —C(O)(C$_{1-6}$alkyl)(aryl), —C(O)OR$^4$; X is selected from —NR$^2$R$^3$, —P(O)(OH)$_2$ or —S(O)$_{n1}$R$^1$; R$^1$ is H or C$_{1-6}$alkyl; R$^2$ is H or C$_{1-6}$alkyl; R$^3$ is H or C$_{1-6}$alkyl; R$^4$ is H or C$_{1-6}$alkyl; n1 is 0-4 are suitable for use herein. Suitable cations or dications for the ionized form(s) of the prodrugs include metal salts or organic amine cations including meglumine salts and the like (N-methyl D-glucamine). Such prodrugs may be utilized with or without the described parenteral delivery vehicles in a suitable liquid formulation to treat patients in need of treatment thereof. Such prodrugs are converted to the non-prodrug form of the drug (or salt thereof) upon parenteral administration to the patient. Such prodrugs may be in amorphous form or in crystalline and/or crystalline solvate/hydrate form.

NK-1 receptor antagonists have been shown to be useful therapeutic agents, for example, in the treatment of pain, inflammation, migraine, nausea, emesis (vomiting), and nociception.

SUMMARY OF THE INVENTION

The present invention broadly relates to formulations suitable for intravenous administration to a patient in need of treatment thereof wherein said formulations comprise a compound of Formula I and pharmaceutically acceptable salts, hydrates, solvates thereof and a vehicle selected from the group consisting of water soluble organic solvents, non-ionic surfactants, water insoluble lipids, organic lipids/semisolids and phospholipids. Water soluble organic solvents may be selected from, for example, polyethylene glycol 300, polyethylene glycol 400, ethanol, propylene glycol, glycerin, N-methyl-2-pyrrolidone, dimethylacetamide and dimethylsulfoxide. Non-ionic surfactants may be selected from Cremophor EL, Cremophor RH 40, Cremophor RH 60, d-α-tocopherol polyethylene glycol 1000 succinate, polysorbate 80, Solutol HS 15, sorbitan monooleate, poloxamer 407, Labrifil M-1944CS, Labrafil M-2125CS, Labrasol, Gellucire 44/14, Softigen 767, and mono- and di-fatty acid esters of PEG 300, 400 or 1750. The water insoluble lipids are selected from castor oil, corn oil, cottonseed oil, olive oil, peanut oil, peppermint oil, safflower oil, sesame oil, soybean oil, hydrogenated vegetable oils, hydrogenated soybean oil, and medium chain triglycerides of coconut oil and palm seed oil. Organic liquids and semisolids may be selected from beeswax, d-α-tocopherol, oleic acid and medium chain mono- and diglycerides. The phospholipids are selected from lecithin, hydrogenated soy phosphatidylcholine, distearoylphosphatidylglycerol, L-α-dimyristoylphosphatidylcholine and L-α-dimyristoylphosphatidylglycerol and others as disclosed herein. The formulations are made to provide sufficient solubility and chemical stability which is defined as <5-10% degradation over one year (preferably two years) under the specified storage conditions which vary depending upon the particular formulation, location etc. Preferably, the formulations are useful as intravenous formulations. As necessary or prescribed, the formulations may also be used broadly as parenteral formulations suitable for delivery by means known in the art including intravenous (IV), intramuscular (IM) or subcutaneous (SC) administration. The prodrugs may be used in oral form or in parenteral formulations comprising an aqueous/saline delivery system with or without the optional delivery vehicles recited above.

The present invention describes and claims inter alia pharmaceutical compositions and formulations of Compound 1 and pharmaceutically acceptable salts thereof for use in treating nausea and/or emesis. The preferred form of Compound 1 used to formulate the compositions recited herein including the iv formulations is as the crystalline monohydrate hydrochloride salt. Development of the claimed formulations required substantial experimentation and effort as described below and in the Examples to overcome the problem of low drug solubility and, in particular, the problem of hemolysis (the alteration, dissolution or destruction of the red blood cells leading to blood leakage in the urine) believed to be caused by a transient, local free concentrations of some form of Compound 1 when intravenously administered via the bolus route to experimental mammals. Hemolysis of the blood does not occur upon administration of conventional oral dosage forms of Compound 1. Hemolysis, in most cases, also does not occur when orally or very slowly administered to the mammal but did occur during either slow infusion and/or bolus administration with certain formulations.

A difficulty initially encountered in developing a formulation of Compound 1 for intravenous administration was that Compound 1 has low solubility at the physiological pH of 7.4 (<4 mcg/ml) and thus, required solubility enhancement to reach therapeutic plasma concentration levels in the body and at an anticipated dose of 100 mg. In addition, it was desired to increase the drug concentration and the dose in the formulation as this would serve to allow reduction of the infusion volume administered to patients.

To solve the problem of low solubility of Compound 1 at physiological pH, studies were undertaken to ascertain which solvent systems would enhance solubility of Compound 1. Captisol® (a β-cyclodextrin derivative also referred herein as Captisol) and co-solvent-based formulations containing propylene glycol and ethanol significantly enhanced solubility of Compound 1. The co-solvent formulations, however, upon intravenous administration unexpectedly caused hemolysis. Further attempts to reduce/minimize the incidence of hemolysis observed with intravenous administration of Captisol formulations of Compound 1, by varying Captisol's concentration, volume, rate of administration or addition of buffers, or utilizing various combinations of ethanol, propylene glycol and polyethylene glycol 400 were successful in some cases. For example, a Captisol formulation administered by infusion over a 15 minute period to rats at doses of 10 mg/kg and 5 mg/kg and with a dose volume of 10 ml/kg (Dose Concentration 1 mg/mL and 0.5 mg/mL respectively) gave a low incidence of hemolysis (1/5). In addition, bolus administration of a Captisol formulation at a dose of 10 mg/kg and in a dose volume of 5 ml/kg (dose concentration 2 mg/ml) caused hemolysis in 2/5 rats. Bolus administration of Captisol at a lower concentration (e.g. comparable to the infusion concentrations of 1 mg/ml and 0.5 mg/ml) could likely lead to even less hemolysis. It was hypothesized that transient local high free concentration of Compound 1 at the injection site may be the main cause of hemolysis.

In order to test the above hypothesis, studies were performed in rats by intravenously administering (slow hand bolus 1-2 minutes) a micelle formulation containing macrogol 15-hydroxystearate (Solutol® HS15, also referred herein as Solutol) (10 mg/mL drug, 22% Solutol HS15, 20 mM Phosphate buffer, pH 7.0) and testing for the incidence of hemolysis at various time intervals and with varying doses (10 mg/kg; 20 mg/kg; and 30 mg/kg) after dosing. It was observed that the incidence of hemolysis in rats reduced significantly 30-60 minutes after dosing versus the 15 minutes dosing period. This result in combination with the fact that Compound 1 possesses high oral availability led to the conclusion that local high free concentration of Compound 1 was responsible for the transient hemolysis which occurred within the first 30 minutes after intravenous dosing.

To minimize/reduce hemolysis associated with Compound 1 a strategy was explored, which was based on the assumption that a slow rate of drug administration would lead to a lower incidence of hemolysis. This involved experiments administering micellar (7.5% Solutol, 25 mg/kg; 5 ml/kg; 5 mg/ml)) solutions of Compound 1 to rats by a 15-minute slow infusion as well as by the bolus mode of administration. A high rate of incidence of hemolysis was observed in rats when the micellar formulation was administered via the bolus mode of administration (5/5), whereas no hemolysis was observed via the infusion route (0/10).

Thus, decreasing the concentration of Solutol in the micellar formulation of Compound 1 from 22% to, for example, 7.5%, and administering the formulation by slow infusion to rats reduced the incidence of hemolysis. However, at the bolus route of administration for the 7.5% Solutol formulation (e.g. a low concentration of Solutol), hemolysis was observed as indicated above. Thus some of the claimed formulations recited herein are suitable for slow infusion but not for bolus administration. Other formulations as further described below are suitable for both slow infusion and bolus administration.

Further experimentation on the Solutol formulation was conducted to evaluate the addition of various types of oils, percentage of oil incorporation, and pH range of the Solutol formulation, on the occurrence of hemolysis in rats. It was believed that the addition of oil to the micellar solution to form microemulsions, i.e., oil-loaded micelles, would additionally serve to retard release of Compound 1 from the hydrophobic core and prevent quick partitioning/transfer of Compound 1 to the red blood cells.

The present invention relates to parenteral formulations comprising, a) a compound of formula I or a pharmaceutically acceptable salt thereof,

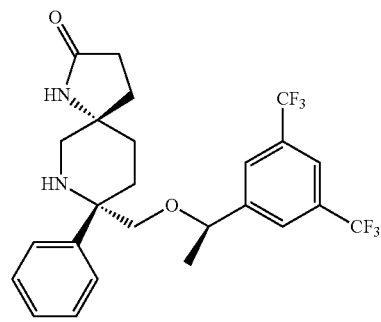 [SMILES: C[C@@H](OC[C@@]1(c2ccccc2)CC[C@]2(CCC(=O)N2)CN1)c1cc(C(F)(F)F)cc(C(F)(F)F)c1]

and b) a pharmaceutically acceptable vehicle.

The term "pharmaceutically acceptable vehicle" means any suitable component which enhances the solubility of a compound of formula I or a pharmaceutically acceptable salt thereof in order to facilitate the parenteral delivery of a therapeutic concentration of such compound or salt to the target NK-1 receptor site(s). The vehicles are selected from the group consisting of cremophors, emulsions, microemulsions, micelles, negatively charged micelles, oil loaded micelles, intralipids, HSA, liposomes and negatively and positively charged amino acids and the like as additionally described herein. Pharmaceutically acceptable vehicles do not include β-cyclodextrin formulations. In the case of liposomes, emulsions, micelle and oil-loaded micelles, it is believed that such vehicles would hold the drug inside the lipophilic core for enhanced drug retention while also shielding the drug in the core. Human Serum albumin based formulations relate to the strong binding of HSA to Compound 1 and which would minimize the partitioning of free drug into red blood cells. Such formulations could be co-formulated with Solutol, Myglyol and vitamin E. Negatively charged amino acids would complex with and neutralize a portion of Compound 1 that retains a positive charge and thus prevent the partitioning of Compound 1 into red blood cells. The positively charged amino acids would complex with a negatively charged portion of Compound 1 and neutralize it and reduce exposure of the compound to red blood cells. A negatively charged micelle would repel the negatively charged erythrocytes and prevent contact of Compound 1 with red blood cells.

The term "micelle formulation" means that the formulation is in the form of a micelle and is derived from or made up of any component which forms or can form a micelle in a pharmaceutically acceptable delivery system such as water, saline, dextrose water, and the like.

The term "emulsion formulation" means that the formulation is in the form of an emulsion and which is derived from or made up of any component which forms or can form an emulsion when presented in and/or combined with a pharmaceutically acceptable delivery system such as water, saline, dextrose water and the like. The preferred emulsion formulations which avoid any hemolytic effects upon bolus or slow infusion administration have an oil content of about 10% or less. The drug concentration can be varied from about 1 mg/mL to about 30 mg/mL with less volume and higher concentration being preferred for intravenous delivery. The pharmaceutical compositions can be prepared to increase or enhance the solubility of the NK-1 antagonist and can also be diluted significantly to avoid any possible hemolytic results but some dilution volumes may be impractical to administer to a patient in need of treatment thereof.

An emulsion formulation or micelle formulation of the present invention additionally comprises an active pharmaceutical ingredient selected from a compound of formula I or Ia and/or pharmaceutically acceptable salts, hydrates, polymorphs or physical forms thereof. Such drug loaded emulsion or micelle formulations may additionally contain excipients which facilitate delivery and/or are useful to prevent or mitigate factors such as hemolysis. Such additional excipients can thus include, for example, oils or other components which enhance or further enhance solubility while mitigating any potential hemolytic effects.

Such emulsion formulations or micelle formulations may be further processed to form more stable physical forms or solutions and can be further processed to, for example, provide sterilized parenteral solutions.

The present invention also relates to parenteral formulations comprising a compound of formula I or a pharmaceutically acceptable salt thereof in the form of a nanoparticle. The nanoparticles of a compound of formula I or salt thereof may then be incorporated in a solution to deliver such nanoparticle by intravenous means. The nanoparticles of compound 1 and pharmaceutically acceptable salts thereof may further include a pharmaceutically acceptable vehicle. It is believed that slow dissolution of such nanoparticles (~200 nm) would result in less hemolysis due to less dissolved drug in a solubilized fraction.

The present invention also relates to a method of delivering a compound of formula I and pharmaceutically acceptable salts thereof to a patient comprising (a) combining a compound of formula I or pharmaceutically acceptable salt thereof with a pharmaceutically acceptable vehicle to form an intravenous formulation (b) delivering the parenteral formulation to a patient in need of treatment thereof.

After considerable trial and efforts by the inventors to solve the aforementioned problems with respect to a Solutol containing formulation, it has been found that the addition of both a medium chain and a long chain oil in a specific ratio to the Solutol yields a solubilized, stable (chemically and physically) microemulsion formulation of Compound 1 which when intravenously administered to experimental mammals results in minimal hemolysis.

In one aspect, the present invention relates to a pharmaceutical composition suitable for parenteral administration, comprising:
  a) a compound of formula I or pharmaceutically acceptable salt thereof

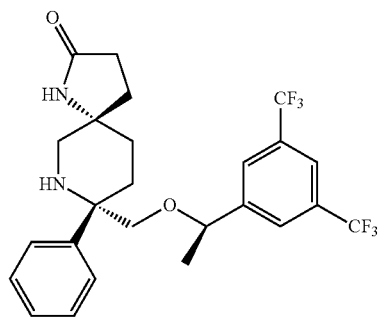 [SMILES: C[C@@H](OC[C@@]1(c2ccccc2)CC[C@]2(CCC(=O)N2)CN1)c1cc(C(F)(F)F)cc(C(F)(F)F)c1]

and
  b) a solubilizer selected from the group consisting of an oil-loaded micelle or a microemulsion.

A preferred embodiment of the invention comprises a pharmaceutical intravenous formulation which comprises:
  a) a compound of Formula I or a pharmaceutically acceptable salt thereof

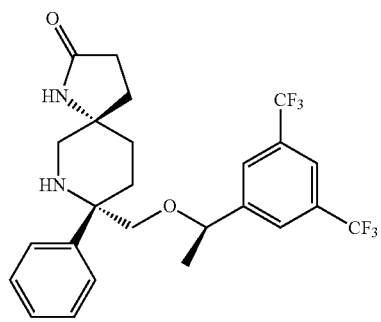 [SMILES: C[C@@H](OC[C@@]1(c2ccccc2)CC[C@]2(CCC(=O)N2)CN1)c1cc(C(F)(F)F)cc(C(F)(F)F)c1]

and
  b) an emulsifier.

The invention also comprises an intravenous formulation comprising a compound of Formula I or a pharmaceutically acceptable salt thereof and human serum albumin (HSA).

The invention also comprises an intravenous formulation comprising a compound of Formula I or a pharmaceutically acceptable salt thereof wherein the compound or salt thereof is in the form of a nanoparticle.

The invention additionally comprises an intravenous formulation comprising a compound of Formula I or a pharmaceutically acceptable salt thereof and a delivery vehicle selected from Cremophor.

The invention further comprises an intravenous formulation comprising a compound of Formula I or a pharmaceutically acceptable salt thereof and a delivery vehicle selected from a micelle.

The invention further comprises an intravenous formulation comprising a compound of Formula I or a pharmaceutically acceptable salt thereof and a delivery vehicle selected from a liposome.

The invention preferably relates to an intravenous emulsion formulation which is suitable for both bolus and infusion administration.

A preferred embodiment of the invention comprises an intravenous formulation comprising a compound of Formula I or a pharmaceutically acceptable salt thereof and at least one emulsifier wherein an emulsion is formed and subject to microfluidization to form droplets having less than 500 nm median diameters and/or a $D_{90}$ of about 600 nm or less.

The invention further relates to an intravenous formulation comprising a compound of Formula I or a pharmaceutically acceptable salt thereof and a negatively or positively charged amino acid.

The invention further comprises an intravenous formulation comprising a compound of Formula I or a pharmaceutically acceptable salt thereof which is lyophilized.

The invention further comprises an intravenous formulation comprising a compound of Formula I or a pharmaceutically acceptable salt thereof in the form of a powder. The powder is reconstituted or added to a liquid to form a liquid intravenous formulation comprising a compound of Formula I or salt thereof which is administered to a patient in need of treatment thereof. Emulsifiers such as Polysorbate 80 (Tween 80) and the like may be added to this formulation as well as other inactive ingredients such as pH adjusters, preservatives (EDTA) etc.

In each of the above embodiments, the preferred form of the compound of Formula I or a salt thereof added to the formulation is as the solid crystalline monohydrate hydrochloride salt.

In each of the above embodiments, an alternative form of the compound of formula I or a salt thereof is selected from a pro-drug of a compound of formula I. Such pro-drugs may be administered by any delivery means including via an oral route or by intravenous administration.

Such pro-drug may be selected from a compound of Formula Ia and pharmaceutically acceptable salts thereof:

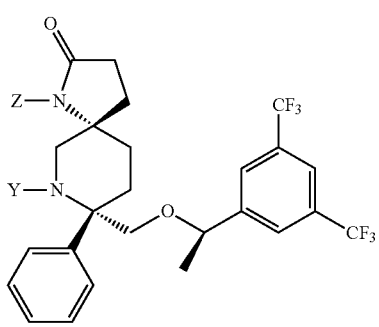 [SMILES: C[C@@H](OC[C@@]1(c2ccccc2)CC[C@]2(CCC(=O)N2)CN1)c1cc(C(F)(F)F)cc(C(F)(F)F)c1]

Ia wherein Z and Y are independently selected from the group consisting of H, —PO(OH)O⁻ M⁺, —PO(O⁻)₂2M⁺, —PO(O⁻)₂D²⁺, —[C(R¹)(R²)]ₙ—PO(OH)O⁻M⁺, —[C(R¹)(R²)]ₙ—PO(O⁻)₂2M⁺, —[C(R¹)(R²)]ₙ—PO(O⁻)₂D²⁺, —C(O)[C(R¹)(R²)]ₘ—OPO(O⁻)₂2M⁺, —C(O)[C(R¹R²)]ₒNR¹R², —C(O)[C(R¹)(R²)]ₚCO₂_M⁺, —SO₃_M⁺, —[C(R¹)(R²)]qSO₃_M⁺ and —[C(R¹)(R²)]ᵣOC(O)OR³, wherein R³ is selected from the group consisting of

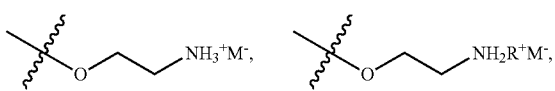

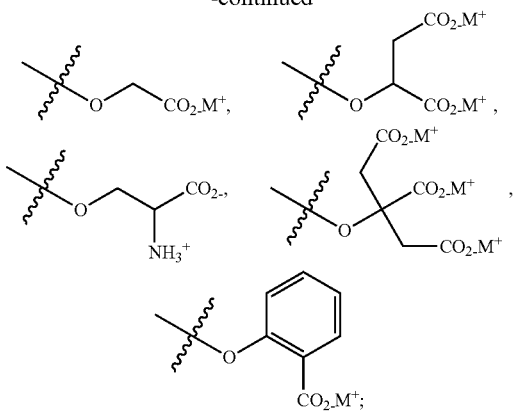

with the proviso that Z and Y cannot both be H; M⁺ is selected from a monovalent cation; D⁺ is selected from a divalent cation; R¹ and R² are independently selected from H or $C_{1-6}$alkyl; n is 1-4; m, o, and p are independently selected from 0-4; and R is selected from $C_{1-6}$alkyl.

In a preferred embodiment of the pro-drug, Z is selected from H and Y is selected from any one of the groups shown above for Z and Y exclusive of H. In a more preferred embodiment, such pro-drugs are selected from:

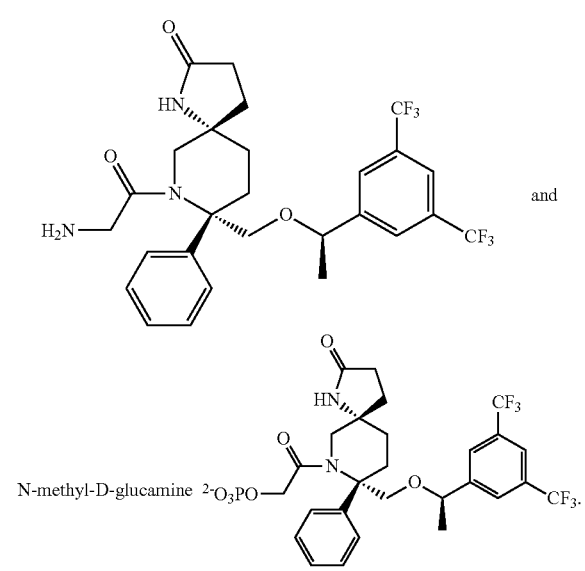

The preferred M⁺ salts are selected from, for example, ammonium salts, alkali metal salts such as sodium, alkaline earth metal salts such as calcium and magnesium, salts with organic bases such as N-methyl-D-glucamine or dicyclohexylamine, amino acid salts such as arginine, lysine and the like.

The pro-drugs are made by reacting the amine or suitably protected amine with an activated group Z—X or Y—X or by any conventional means to form the pro-drug variant of a compound of formula I.

The prodrugs of the instant invention possess enhanced solubility over the parent drug and are thus useful and suitable for intravenous administration.

A preferred embodiment of the invention is a pharmaceutical composition which comprises:

a) a compound of Formula I

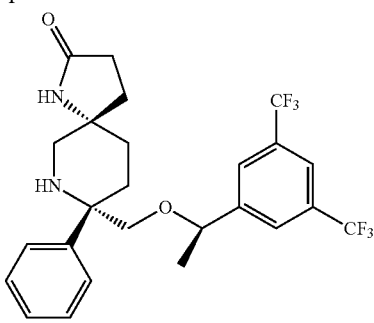

or a pharmaceutically acceptable salt thereof;
b) macrogol 15-hydroxystearate in an amount of from about 0.50% to about 10.0% by weight of the total composition;
c) a medium chain triglyceride in an amount of from about 0.10% to about 2.5% by weight of the total composition;
d) a long chain triglyceride in an amount of from about 0.10% to about 1.5% by weight of the total composition; and
e) at least one buffer, wherein the weight ratio of macrogol 15-hydroxystearate:medium chain triglyceride:long chain triglyceride in the composition is about 5-100:1-5:1, and
wherein the pH of the composition is from about 6.5 to about 8.0.

The above formulation may be in the form of an oil-loaded micelle or microemulsion.

In another embodiment, the invention provides a pharmaceutical composition which comprises macrogol 15-hydroxystearate in an amount of from about 0.50% to about 7.5% by weight of the total composition; a medium chain triglyceride in an amount of from about 0.15% to about 1.5% by weight of the total composition; and a long chain triglyceride in an amount of from about 0.10% to about 1.2% by weight of the total composition.

In another embodiment, the invention provides a pharmaceutical composition which comprises macrogol 15-hydroxystearate in an amount of from about 0.88% to about 4.84% by weight of the total composition; a medium chain triglyceride in an amount of from about 0.20% to about 1.20% by weight of the total composition; and a long chain triglyceride in an amount of from about 0.10% to about 0.75% by weight of the total composition.

In another embodiment, the invention provides a pharmaceutical composition which comprises:
(a) a compound of Formula I

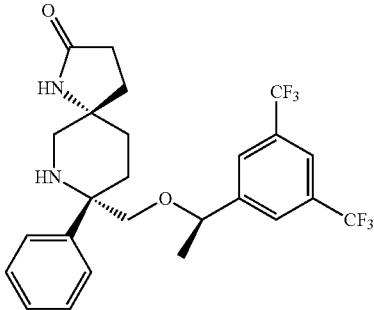 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
(b) macrogol 15-hydroxystearate in an amount of about 4.4% by weight of the total composition;
(c) at least one medium chain triglyceride in an amount of about 1.1% by weight of the total composition;
(d) refined soybean oil in an amount of about 0.66% by weight of the total composition; and
(e) a phosphate buffer, wherein the pH of the composition is about 7.5.

In another embodiment, the invention provides a pharmaceutical composition which comprises:
(a) a compound of Formula I

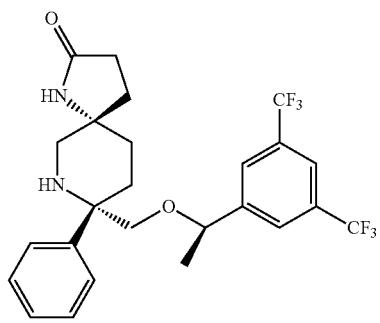 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
(b) macrogol 15-hydroxystearate in an amount of about 0.88% by weight of the total composition;
(c) at least one medium chain triglyceride in an amount of about 0.22% by weight of the total composition;
(d) refined soybean oil in an amount of about 0.12% by weight of the total composition; and
(e) a phosphate buffer, wherein the pH of the composition is about 7.5.

In another aspect, the invention provides a process for making a pharmaceutical composition which comprises:
a) heating (i) melted macrogol 15-hydroxystearate, (ii) a medium chain triglyceride and (iii) a long chain triglyceride to form a composition;
b) adding water to the composition to form a microemulsion composition;
c) adding to the microemulsion composition a compound of Formula I

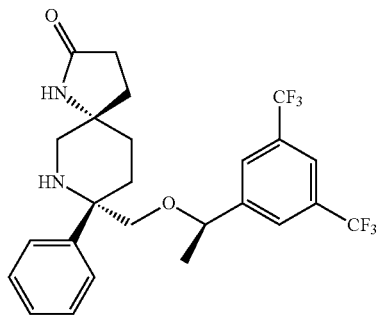 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and
d) adding at least one buffer and adjusting the pH from about 6.5 to about 8.0 to form a pharmaceutical composition, wherein the macrogol 15-hydroxystearate is present in an amount of from about 0.50% to about 10.0% by weight of the total pharmaceutical composition, the medium chain triglyceride is present in an amount of from about 0.10% to about 2.5% by weight of the total pharmaceutical composition, and the long chain triglyceride is present in an amount of from about 0.10% to about 1.5% by weight of the total pharmaceutical composition, and wherein the weight ratio of macrogol 15-hydroxystearate:medium chain triglyceride:long chain triglyceride in the pharmaceutical composition is about 5-100:1-5:1.

In another aspect, the invention provides a pharmaceutical composition which comprises:

a) a compound of Formula I

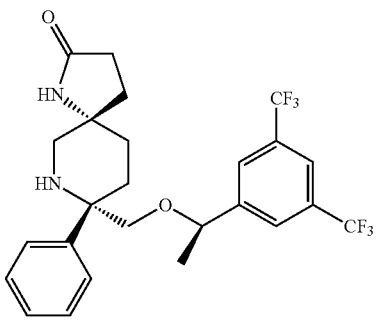 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and b) pegylated hydroxystearate in an amount of from about 0.88% to about 5.0% by weight of the total composition, wherein the pegylated hydroxystearate is substantially free from free polyethylene glycol, and wherein the pH of the composition is from about 6.5 to about 8.

In another aspect, the invention provides a method for treating nausea and/or emesis in a patient in need of treatment which comprises intravenously administering by infusion to the patient an effective amount of a pharmaceutical composition of the present invention, wherein hemolysis in the patient is minimized.

In another aspect, the invention provides a method for minimizing hemolysis in a patient following intravenous administration of a compound of the formula I or a pharmaceutically acceptable salt thereof,

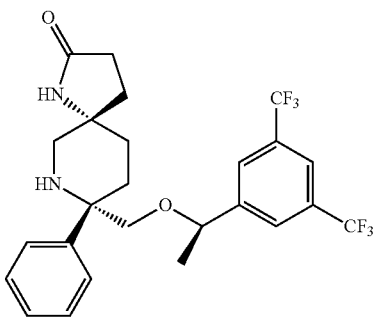

the method comprising intravenously administering by infusion to the patient an effective amount of a pharmaceutical composition of the present invention.

In another embodiment, the recited intravenous formulations may be used in combination with other antiemetic and antinausea medications; anti-inflammatory or steroidal agents (e.g. dexamethasone) and with chemotherapeutic agents. The recited intravenous formulations may be given to the patient according to the prescription and regimen provided by a physician. Such other medications include ondansetron and other known $5HT_3$ antagonists. Thus, a compound of formula I and salts thereof for injection may be utilized with other antiemetic agents for the prevention of acute and delayed nausea and vomiting associated with initial and repeat courses of highly emetogenic cancer chemotherapy including, for example, treatment with cisplatin. A compound of formula I and salts thereof for injection may also be utilized with other antiemetic agents for the prevention of acute and delayed nausea and vomiting associated with initial and repeat course of moderately emetogenic cancer chemotherapy. In addition to treatment with cisplatin, other anticancer agents that are administered in this combination dosing regimen include etoposide, flurouracil, gemcitabine, vinorelbine, paclitaxel, cyclophosphamide, doxorubicin, docetaxel and can also include temozolomide. The treatment with a compound of formula I should begin thirty minutes before chemotherapy treatment on day 1 of such treatment. The i.v. formulation may be administered by slow infusion over fifteen minutes or by bolus injection depending upon the formulation.

In another embodiment, the i.v. formulations of a compound of Formula I and a pharmaceutically acceptable salt thereof may be administered alone or in combination with other agents for the treatment and/or prevention of post operative nausea and vomiting. Such combination agents include other antiemetic therapeutic agents such as ondansetron and other $5HT_3$ antagonists.

DETAILED DESCRIPTION OF THE INVENTION

Figure 1:
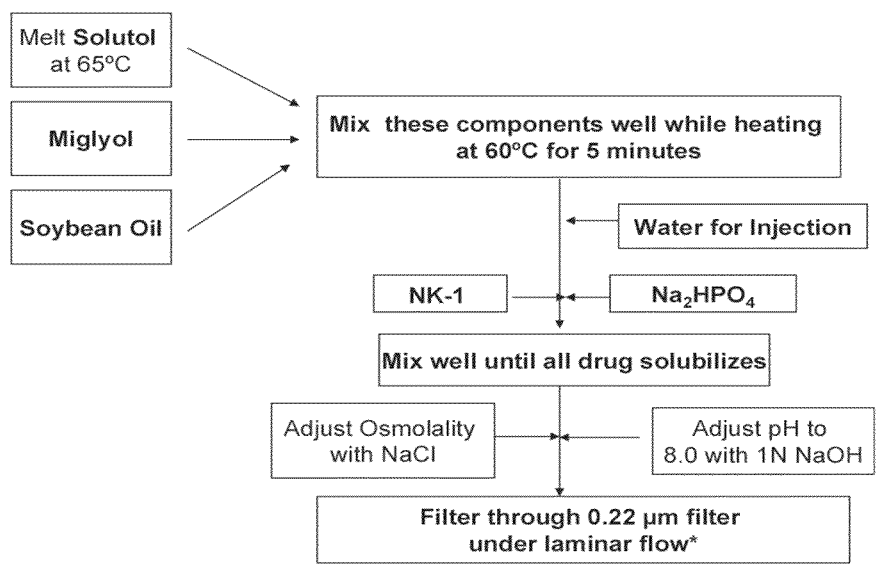
FIG. 1. Preparation of intravenous microemulsion formulations of Compound 1 (schematic flow chart).

As used herein, the following terms, unless otherwise indicated, are understood to have the following meanings:

The term "micelle" or "micellar" as used herein refers to a colloidal aggregate of amphiphilic molecules (surfactants), which occurs at or above a well-defined concentration called the critical micelle concentration. Macrogol 15-hydroxystearate (Solutol® HS15, available from BASF Ludvigshafen, Germany) is a specific example of a surfactant with a critical micellar concentration in the range of 0.005% to 0.02%.

The term "microemulsion" as used herein refers to a clear, stable, isotropic liquid mixture of oil, water and the surfactant. This term also means an oil-loaded micelle.

The term "hemolysis" as used herein means destruction of red blood cells which leads to the release of hemoglobin from within the red blood cells into the blood plasma. Hemolysis can be measured by methods well known in the art, e.g., Hemastix® reagent strips (Bayer Corp., Elkhart, Ind.) which detect blood in urine. The Hemastix® reagent strips turn from yellow to dark green depending upon the amount of hemoglobin found in the urine. The Hemastix® scale is as follows: 0=negative, 1=non-hemolyzed trace, 3=hemolyzed trace, 4=small+, 5=moderate++, and 6=large+++.

The phrases "minimal hemolysis" and "hemolysis is minimized" as used herein means that upon administration in experimental mammals of a formulation of Compound 1, either no hemolysis has been observed in the experimental mammals or no more than two experimental mammals out of ten experimental mammals exhibit a trace level of hemolysis, as measured, e.g., on the Hemastix® scale as three or less.

The term "stable" as used herein refers to both chemical and physical stability.

Physical stability refers to micelles and microemulsions that show no significant difference in the particle size/droplet size and do not show any phase separation.

Chemical stability as used herein pertains to the maintenance of active potency of Compound 1 in the allowable range (greater than 90% of labelled strength).

The term "effective amount" as used herein refers to the amount of Compound 1 or pharmaceutically acceptable salt thereof that will prevent, improve or reduce nausea and/or emesis in a patient, e.g., a mammal such as a human or non-human primate or a companion animal such as a dog or a cat.

The term "treat", "treating" or "treatment" as used herein refers to prevention or improvement or reduction of nausea and/or emesis.

The term "about" as used herein will be understood by persons of ordinary skill in the art to mean up to plus or minus 10% of the particular term.

The present invention is directed to pharmaceutical compositions in the form of microemulsions for intravenous administration comprising a compound of Formula I (also referred herein as Compound 1), Formula I

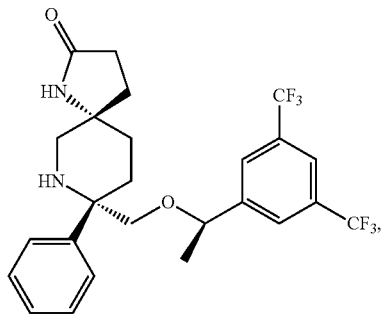

methods for preparing the pharmaceutical compositions and methods for treating nausea and/or emesis utilizing the pharmaceutical compositions.

In contrast to the co-solvent formulations of Compound 1 that when tested in experimental mammals caused hemolysis, the problem of hemolysis caused by intravenous administration of Compound 1 was successfully resolved in experimental mammals by a pharmaceutical composition of the present invention which comprises from about 0.50% to about 10.0% of Solutol, from about 0.10% to about 2.5% of a medium chain triglyceride and from about 0.10% to about 1.5% of a long chain triglyceride, wherein the weight ratio of macrogol 15-hydroxystearate:medium chain triglyceride:long chain triglyceride in the composition is about 5-100:1-5:1. Without being bound by any particular mechanism of action of the solvent system, it is thought that intravenous administration of the pharmaceutical composition results in significantly reduced hemolysis by reducing the transfer rate of Compound 1 from the micellar core to the red blood cells. The preferred concentration was in the range of 1-15 mg/mL.

The problem of hemolysis caused by intravenous administration of Compound 1 was also solved utilizing a formulation comprising pegylated hydroxystearate alone in a particular concentration range, wherein the pegylated hydroxystearate was substantially free of free polyethylene glycol.

In one aspect, the present invention provides a pharmaceutical composition comprising:
a) a compound of Formula I

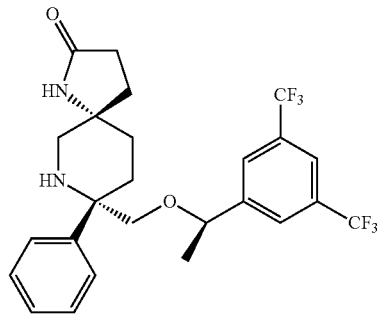

or a pharmaceutically acceptable salt thereof;
b) macrogol 15-hydroxystearate (Solutol® HS15) in an amount of from about 0.50% to about 10.0% by weight of the total composition;
c) a medium chain triglyceride in an amount of from about 0.1% to about 2.5% by weight of the total composition;
d) a long chain triglyceride in an amount of from about 0.10% to about 1.5% by weight of the total composition; and
(e) at least one buffer, wherein the weight ratio of macrogol 15-hydroxystearate:medium chain triglyceride:long chain triglyceride in the composition is about 5-100:1-5:1, and
wherein the pH of the composition is from about 6.5 to about 8.0.

The composition of the present invention is surprisingly associated with minimal hemolysis when intravenously administered by infusion to a patient.

The compound of Formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. In some embodiments, the compound of Formula I is present as a hydrochloride salt. The salts are prepared by contacting the free base form with a sufficient amount of the desired acid to produce a salt in a conventional manner.

In some embodiments, the compound of Formula I or pharmaceutically acceptable salt thereof is present in the pharmaceutical composition in a concentration of from 1 mg/ml to 15 mg/ml, from 2.0 mg/ml to 10 mg/ml, or 2.0 mg/ml of the total composition.

Macrogol 15-hydroxystearate (Solutol® HS15, available from BASF Ludvigshafen, Germany) is a surfactant with a critical micellar concentration in the range of 0.005% to 0.02%. Without intending to be limited to any particular mechanism of action, the inventors believe that a concentration above its critical micelle concentration results in the formation of micelles that provide a hydrophobic environment to encapsulate Compound 1 and reduce exposure of Compound 1 to the red blood cells. Solutol® HS15 is present in the pharmaceutical composition in an amount of from about 0.50% to about 10.0% by weight of the total composition.

Suitable medium chain triglycerides include, but are not limited to, caprylic acid triglyceride, capric acid triglyceride, and caprylic/capric acid triglyceride sold as propylene glycol dicaprylate/dicaprate —MIGLYOL® 812 or MIGLYOL® 810 by SASOL North America; trigylceride from coconut oil sold as CAPTEX 300/CAPTEX 850® by Abitech Corp; caprylic/caprylic triglyceride sold as CAPTEX 355® by Abitech Corp; caprylic/caprylic/lauric triglyceride sold as CAPTEX 350® by Abitech Corp; caprylic/caprylic/linoleic triglyceride sold as CAPTEX 810® by Abitech Corp; caprylic/caprylic/stearic triglyceride sold as CAPTEX SBE® by Abitech Corp and combinations of two or more thereof. The medium chain triglyceride is present in the pharmaceutical composition in an amount of from about 0.1% to about 2.5% by weight of the total composition.

Suitable long chain triglyercerides and/or long chain fatty acids include, but are not limited to, soybean oil sold as SUPER-REFINED SOYBEAN OIL USP® by Croda; corn oil sold as SUPER-REFINED CORN OIL NF® by Croda; cottonseed oil sold as SUPER-REFINED COTTONSEED OIL NF® by Croda; olive oil sold as SUPER-REFINED OLIVE OIL NF® by Croda; peanut oil sold as SUPER-REFINED PEANUT OIL BF® by Croda; safflower oil sold as SUPER-REFINED SAFFLOWER USP® by Croda; sesame oil sold as SUPER-REFINED SESAME NF® by Croda; shark liver oil sold as; SUPER-REFINED SHARK LIVER® by Croda; ethyl oleate sold as Crodamol EO® by Croda, castor oil, monounsaturated omega-9 fatty acid sold as Oleic acid by Croda and combinations of two or more thereof. The long chain triglyceride or long chain fatty acid or both is present in the pharmaceutical composition in an amount of from about 0.10% to about 1.5% by weight of the total composition.

In an embodiment, the invention provides a pharmaceutical composition which comprises macrogol 15-hydroxystearate in an amount of from about 0.50% to about 7.5% by weight of the total composition; a medium chain triglyceride in an amount of from about 0.15% to about 1.5% by weight of the total composition; and a long chain triglyceride in an amount of from about 0.10% to about 1.2% by weight of the total composition.

In another embodiment, the invention provides a pharmaceutical composition which comprises macrogol 15-hydroxystearate in an amount of from about 0.88% to about 4.84% by weight of the total composition; a medium chain triglyceride in an amount of from about 0.20% to about 1.20% by weight of the total composition; and a long chain triglyceride in an amount of from about 0.10% to about 0.75% by weight of the total composition.

In another embodiment, the medium chain triglyceride is caprylic/capric triglyceride sold as propylene glycol dicaprylate/dicaprate-MIGLYOL® 810 or MIGLYOL®812 by SASOL North America (Houston, Tex.), and the long chain triglyceride is soybean oil in a super refined form.

The pharmaceutical composition also comprises at least one buffer. Non-limiting examples of suitable buffers which can be included in the pharmaceutical composition include phosphate buffers (pH 7-8) such as sodium phosphate, potassium phosphate and calcium phosphate buffers, succinate buffers (pH 4-6), citrate buffers (pH 2-6), TRIS (pH 7-8) from 5-20 mM and mixtures thereof.

The amount of buffer in the pharmaceutical composition may depend on the type and concentration of buffer. For example, assuming a 10-20 mM phosphate buffer for adjustment between pH 6.5 to 8.0, the phosphate may be added to the composition in an amount of from 0.01% to 0.5% by weight; or about 0.05% to 0.02% by weight or 0.4% to 0.2% by weight, of the total composition. As an example, when a sodium phosphate dibasic anhydrous/monobasic dehydrate system is utilized about 0.2% by weight sodium phosphate monobasic and about 0.284% by weight sodium phosphate dibasic (anhydrous) is added to the composition.

The pH of the composition of the present invention is adjusted, if necessary by means of an alkali such as sodium hydroxide, to a pH of from about 6.5 to about 8.0. In some embodiments, the pH of the composition is from about 7.0 to about 8.0, a pH of about pH 7.5, or a pH of 7.5.

If desired, the pharmaceutical composition of the present invention may further comprise other excipients, e.g., anti-oxidants (preservatives), anti-microbial agents, chelating agents, albumin, tonicity adjustors, bulking agents, etc. As examples, anti-microbial agents are BAC (0.1%-0.025%), benzoic acid (0.1-0.2%), benzyl alcohol (0.0001-1.5%); anti-oxidants are BHT, BHA (0.0001-0.001%), histidine, methionine, glycine, sodium sulphite/bisulfite (0.01-0.2%) and ascorbic acid (0.02-0.2%); chelating agents are EDTA (0.01-1.0%), DTPA (diethylene triamine pentaacetic acid); albumin (0.05-1.2%); tonicity adjustors (NaCl, mannitol (1-10%), glycerol (0.2-2.5%); and bulking agents are mannitol (1-10%), sucrose, glycine (0.1%-2.5%), trehalose, and lactose (0.1-3.0%).

In another embodiment, the invention provides a pharmaceutical composition which comprises:
(a) a compound of Formula I

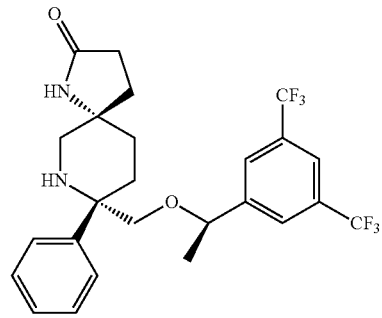 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
(b) macrogol 15-hydroxystearate (Solutol® HS 15) in an amount of about 4.4% or 4.4% by weight of the total composition;
(c) at least one medium chain triglyceride in an amount of about 1.1% or 1.1% by weight of the total composition;
(d) refined soybean oil in an amount of about 0.66% or 0.66% by weight of the total composition; and (e) a phosphate buffer, wherein the pH of the composition is about 7.5.

In a further embodiment, the invention provides a pharmaceutical composition which comprises:
(a) a compound of Formula I

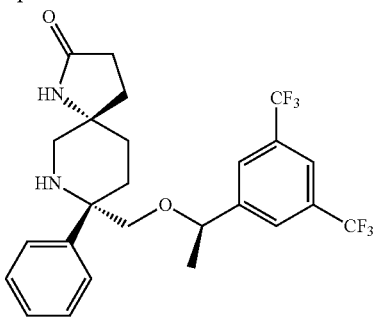

or a pharmaceutically acceptable salt thereof;
(b) macrogol 15-hydroxystearate (Solutol® HS 15) in an amount of about 0.88% or 0.88% by weight of the total composition;
(c) at least one medium chain triglyceride in an amount of about 0.22% or 0.22% by weight of the total composition;
(d) refined soybean oil in an amount of about 0.12% or 0.12% by weight of the total composition; and
(e) a phosphate buffer, wherein the pH of the composition is about 7.5.

Examples of medium chain triglycerides are as described above.

The pharmaceutical composition of the present invention can be sterilized by any of several sterilization techniques including filtration sterilization, and sterilization by autoclaving. In an embodiment, the pharmaceutical composition is sterilized by a filtration method, e.g., utilizing a filter having a pore size from 0.01 to about 0.45 μm, e.g., a 0.22 μm. filter.

Suitably, the pharmaceutical composition of the present invention is chemically and physically stable for 1 to 6 months, typically 3 months at a temperature from 5° C. to 40° C./75% RH (relative humidity).

In another aspect, the present invention provides a process for making the pharmaceutical composition which comprises the steps of:
a) mixing and heating (i) melted macrogol 15-hydroxystearate, (ii) a medium chain triglyceride and (iii) a long chain triglyceride to form a composition;
b) adding water to the composition to form a microemulsion composition;
c) adding to the microemulsion composition a compound of Formula I

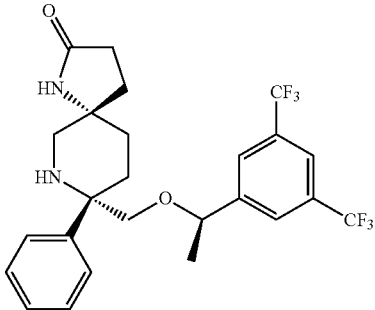 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and d) adding at least one buffer and adjusting the pH from about 6.5 to about 8 to form a pharmaceutical composition, wherein the macrogol 15-hydroxystearate is present in an amount of from about 0.50% to about 10.0% by weight of the total pharmaceutical composition, the medium chain triglyceride is present in an amount of from about 0.10% to about 2.5% by weight of the total pharmaceutical composition, and the long chain triglyceride is present in an amount of from about 0.10% to about 1.5% by weight of the total pharmaceutical composition, and wherein the weight ratio of macrogol 15-hydroxystearate:medium chain triglyceride:long chain triglyceride in the pharmaceutical composition is about 5-100:1-5:1.

Examples of medium chain and long chain triglycerides and concentration of Compound 1 are described above.

As an example of the present process for making the pharmaceutical composition, Solutol® HS15 is melted by heating the Solutol® HS15 at a temperature of 60° C. to 65° C., or at a temperature of about 65° C. The melted Solutol® HS15, medium and long chain triglycerides are mixed at a temperature of 50° C. to 65° C., or at about 60° C. for about 5 minutes to about 15 minutes to form a composition. Water for Injection is then added to form a microemulsion composition followed by the addition of Compound 1 to form a pharmaceutical composition. Sodium monobasic/dibasic phosphate is then added to the pharmaceutical composition. The pH of the pharmaceutical composition is adjusted to a pH of e.g., 7.5 utilizing sodium hydroxide and the tonicity of the composition is adjusted with the tonicity agent, sodium chloride, to approximately 290 mM. Water is then added to the desired volume followed by sterilization of the composition by filtration through a 0.22 μM filter (See infra Example 5).

The process for preparing Compound 1 is described in the '320 patent as preparation of Example 72a and is carried out in 18 individual steps from commercially available starting materials (See the '320 patent at col. 43, line 55 to col. 45, line 20; col. 75, line 55 to col. 80, line 21; col. 90 lines 35 to 63; and col. 98, line 1 to col. 99, line 24, which is herein incorporated by reference. See also WO2008/11833, Examples 1-6, which are herein incorporated by reference).

In another embodiment, the invention provides a pharmaceutical composition which comprises:
a) a compound of Formula I

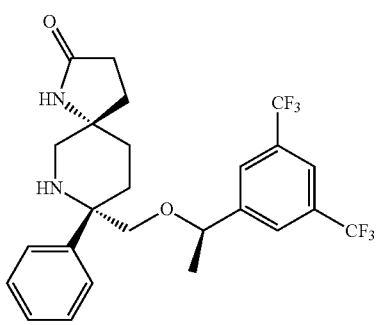 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and
b) pegylated hydroxystearate in an amount of from about 0.88% to about 5% by weight of the total composition, wherein the pegylated hydroxystearate is substantially free from free polyethylene glycol (PEG), and wherein the pH of the composition is from about 6.5 to about 8.0.

The term "substantially free" means that the composition of pegylated hydroxystearate contains no more than 2% free PEG.

To prepare pegylated hydroxystearate substantially free from free PEG, the free PEG contained in pegylated hydroxystearate, e.g., Solutol®HS15, may be removed by techniques known in the art, e.g., dialysis (see infra Example 5, Preparation of Dialyzed Solutol in Phosphate Buffered Saline and Table 9).

The pharmaceutical compositions of the present invention are useful for the treatment of nausea and/or emesis. Accordingly, in another aspect, the present invention provides a method for treating nausea and/or emesis in a patient in need of treatment, e.g., a human or non-human primate such as a monkey or a companion animal such as a dog or a cat. The method comprises intravenously administering by infusion to the patient an effective amount of a pharmaceutical composition of the present invention, wherein hemolysis is minimized upon the intravenous administration of the pharmaceutical composition. The pharmaceutical compositions are useful in treating delayed onset emesis such as that experienced 24 hours to several days after the administration of chemotherapy. See Gonzales et al, Oncology Special Edition, Vol. 5 (2002), p. 53-58. The pharmaceutical compositions are also useful in treating acute nausea and/or emesis induced by chemotherapy, radiation, motion and alcohol (e.g., ethanol), high dose oral antibiotics, viral or bacterial gastroenteritis. The pharmaceutical compositions may also be co-formulated to include at least one other anti-emetic agent, e.g., dexamethasone or ondansetron HCl. The pharmaceutical compositions herein may also be provided in combination with such other anti-nausea and/or emetic agents and/or chemotherapeutic agents as prescribed by a physician.

The pharmaceutical composition can be diluted prior to administration with a suitable aqueous diluent(s) such as normal saline, dextrose, dextrose filtered water and mannitol, to obtain any intermediary composition between about 0.88% to about 4.4% Solutol® HS15 by weight of the total composition.

The dosage regimen utilized for the pharmaceutical composition of the present invention is selected based on consideration of a variety of factors, including species, age, weight, sex and medical condition of the patient in need of treatment, and the severity of the nausea and/or vomiting experienced by the patient. An ordinary skilled physician can readily determine and prescribe the effective amount of Compound 1 to prevent, improve or reduce the nausea and/or emesis. For example, the total daily dosage of the compound of formula I for an adult human is from 1 mg/kg to 9 mg/kg patient body weight or from 1 mg/kg to 3 mg/kg patient body weight (assuming a dose of 200 mg for a 70 kg patient).

The pharmaceutical composition may be intravenously administered by infusion for a period of 15 to 90 minutes, 15 to 60 minutes, or 15 to 30 minutes. In some formulations, the composition may be administered by a bolus injection.

In another aspect, the present invention provides a method for minimizing hemolysis in a patient, e.g., a mammal, such as a human or non-human primate or a companion animal such as a dog or cat, following intravenous administration of a compound of the formula I

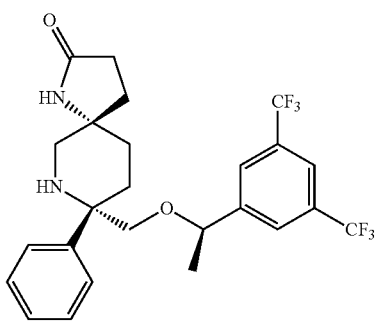 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof, comprising intravenously administering by infusion to the patient an effective amount of a pharmaceutical composition of the present invention.

The present invention relates to a method of treating a patient in need of treatment thereof with an intravenous formulation comprising a compound of Formula I or a pharmaceutically acceptable salt thereof wherein the dosage ranges from 100 to 200 mgs of such compound and the formulation is administered to the patient as a single dose once prior to a chemotherapy or radiation cycle or once prior or post surgery to treat CINV (Chemotherapy Induced Nausea and Vomiting), PONV (Post Operative Nausea and Vomiting) or RINV (Radiation Induced Nausea and Vomiting).

In addition to the Solutol containing formulations described above, the present invention also relates to emulsion formulations which are suitable for both bolus and slow infusion intravenous administration. The compounds useful in such formulations include compounds of formula I and Ia and pharmaceutically acceptable salts thereof.

Parenteral emulsions based upon medium and long chain triglycerides and with additional excipients such as egg lecithins were formulated. Some of these formulations prepared with egg PC and Lipoid E80S resulted in clean (i.e., little or no hemolysis) formulations when administered by both bolus and infusion routes to mammals (rats). The preferred formulations were subject to microfluidization to result in emulsions having smaller droplet size and a relatively narrow particle size distribution (sub 500 nm median diameter and having a $D_{90}$ of less than about 600 nm). Such formulations were also physically stable after sterilization by autoclaving at 121° C.

Thus, in another embodiment, the invention provides a pharmaceutical composition which comprises:
a) a compound of Formula I

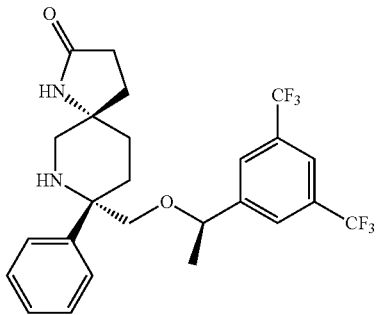 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and
b) a phospholipid.

In another embodiment, the invention provides a pharmaceutical composition which comprises:

a) a compound of Formula I

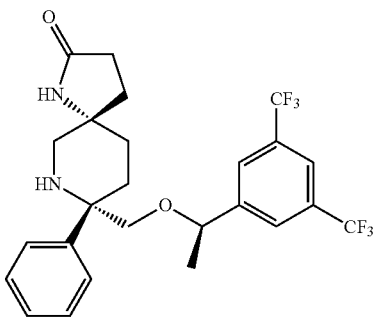 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and b) a long chain fatty acid and/or a long chain triglyceride.

In another embodiment, the invention provides a pharmaceutical composition which comprises:

a) a compound of Formula I

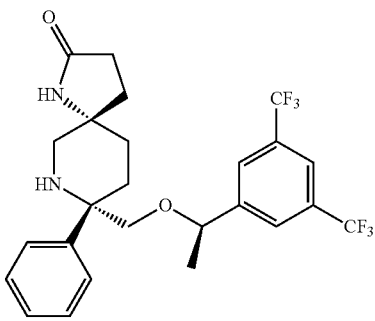 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and b) a medium chain triglyceride.

In another embodiment, the invention provides a pharmaceutical composition which comprises:

a) a compound of Formula I

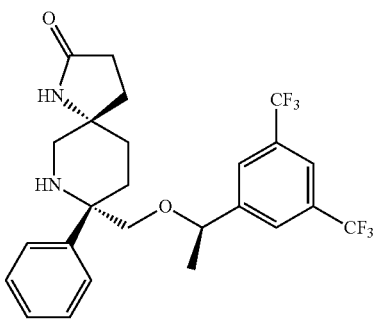 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and b) a medium chain triglyceride and/or long chain fatty acid or triglyceride; and c) a phospholipid.

In another embodiment, the invention provides a pharmaceutical composition which comprises:

a) a compound of Formula I

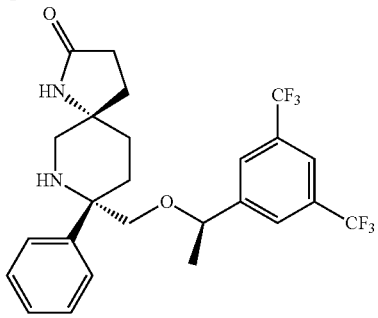 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and b) a medium chain triglyceride and/or long chain fatty acid or triglyceride; and c) a phospholipid and d) glycerin.

In another embodiment, the invention provides a pharmaceutical composition which comprises:

a) a compound of Formula I

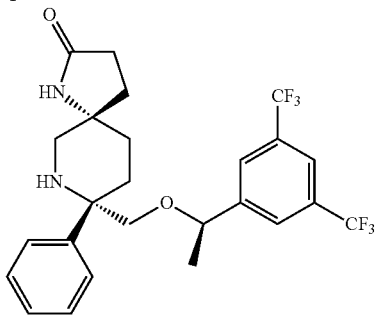

or a pharmaceutically acceptable salt thereof; and b) a medium chain triglyceride and/or long chain fatty acid or tirglyceride; and c) a phospholipid;

d) glycerin and e) ethanol.

In a preferred embodiment, the weight percentage of the oil load (e.g. component(s) b) is about 10% wt/wt based upon the weight of the total composition.

In another embodiment, the invention provides a pharmaceutical composition which comprises:

a) a compound of Formula I

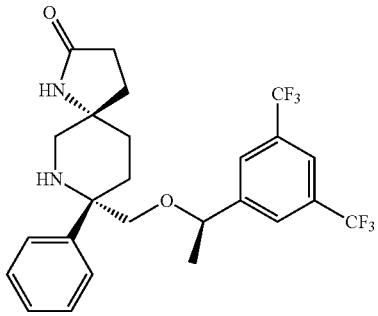 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof; and b) 10% of a medium chain triglyceride and/or long chain fatty acid or triglyceride; and c) 1.2% of a phospholipid and d) 2.25% of glycerin.

In another embodiment of the invention, an effective amount of one or more of the formulations recited herein may be used in combination with other active ingredients either in separate doses and before or after administration of the additional active ingredient (or concurrently therewith) or in fixed combination doses of the NK-1 antagonist in combination with such other active ingredient. The formulations of the invention may be administered in combination with one or more selective serotonin reuptake inhibitors ("SSRIs") to treat depression or anxiety. Representative SSRIs include fluoxetine, fluvoxamine, paroxetine, sertraline and pharmaceutically acceptable salts thereof. In another aspect, the invention relates to a method of treating emesis or delayed onset emesis such as that experienced hours to days after receiving chemotherapy. Combinations of the iv formulations of the present invention with another anti-emetic agent such as a serotonin 5-$HT_3$ receptor antagonist, a corticosteroid or a substituted benzamide can be used to treat other forms of emesis including acute emesis induced by chemotherapy, radiation, motion and/or alcohol (ethanol), and post-operative nausea and vomiting. Examples of 5-$HT_3$ antagonists include palosetron, dolasetron, ondansetron and granisetron or pharmaceutically acceptable salts thereof. An example of a suitable corticosteroid is dexamethasone. An example of a suitable benzamide is metoclopramide. Preferred combinations include combinations of any two of the above or any one of the above with (or within) the NK-1 iv formulation.

The present invention relates to a method of treating acute and delayed nausea and vomiting associated with initial and repeat courses of highly emetogenic cancer chemotherapy comprising administration of an intravenous formulation of a compound of formula I in combination with at least one additional antiemetic agent.

The present invention relates to a method of treating acute and delayed nausea and vomiting associated with initial and repeat courses of moderately emetogenic cancer chemotherapy comprising administration of an intravenous formulation of a compound of formula I in combination with at least one additional antiemetic agent.

The present invention relates to a method of treating acute and delayed nausea and vomiting associated with initial and repeat courses of highly emetogenic cancer chemotherapy comprising administration of an intravenous formulation of a compound of formula Ia in combination with at least one additional antiemetic agent.

The present invention relates to a method of treating acute and delayed nausea and vomiting associated with initial and repeat courses of moderately emetogenic cancer chemotherapy comprising administration of an intravenous formulation of a compound of formula Ia in combination with at least one additional antiemetic agent.

The following examples have been set forth below as a guide to the practitioner and are not meant in any way to limit the scope of the present invention.

Examples

Examples 1-4 describe the development of certain intravenous formulations of Compound 1 or other studies regarding hemolysis. Example 5 provides a description of the development of the intravenous microemulsion (oil-load micelle) formulation of Compound 1 of the present invention. Example 6 provides additional formulations. Example 7 describes an emulsion formulation suitable for both bolus and slow infusion iv administration. Example 8 provides examples of prodrugs.

Example 1

Evaluation of Solubility of Compound 1 in Cyclodextrin-Based and Other Co-Solvent Systems The solubility of Compound 1 in 16% Captisol® (a sulfobutyl ether derivative of 3-cyclodextrin, available from Cydex Inc. of Overland Park, Kans.) and a co-solvent system propylene glycol:ethanol (PG:EtOH, 40%:10%) was evaluated by determining the equilibrium solubility of Compound 1 in these solvent systems. Compound 1 concentration was assayed by the High Performance Liquid Chromatography (HPLC) method as described in Example 5 at difference time points for the determination of equilibrium solubility, which was attained once the solubility reached a plateau (does not change appreciably) over time. Optimal solubility of Compound 1 was found with 16% Captisol (data not shown).

Example 2

Studies in Rats Intravenously Administered NK-1 Formulations Containing Captisol® and Other Co-Solvent Systems 16% Captisol® and the co-solvent system PG:EtOH 40%:10% were intravenously administered to rats.

Urine samples from the rats were assessed for hemolysis using Hemastix® reagent strips (No. 2190, Bayer Corp., Elkhart Ind.). The presence of blood in urine was detected using Hemastix® reagent strips (No. 2190, Bayer Corp., Elkhart Ind.). The Hemastix® reagent strips detect the peroxide-like activity of hemoglobin. The strips turn from yellow to dark green depending upon the amount of hemoglobin found in the urine. The Hemastix® scale is as follows: 0=negative, 1=non-hemolyzed trace, 3=hemolyzed trace, 4=small+, 5=moderate++, and 6=large+++.

Though the cyclodextrin and the co-solvent formulations succeeded in improving solubility of Compound 1, the co-solvent formulations unexpectedly lead to severe hemolysis (on a scale of 6 on the Hemastix® scale) on intravenous infusion administration. The 15 minute slow infusion route with the Captisol formulation led to a lower incidence of hemolysis. (Table 1).

TABLE 1

Captisol ® and Co-Solvent Hemolytic Testing Results on Intravenous Administration

| Formulation | Bolus (B) or Infusion (I) | Dose (mg/kg) | Dose vol (mL/kg) | Dose Conc (mg/mL) | Incidence + hb-uria/sex |
|---|---|---|---|---|---|
| 16% Captisol | I | 10 | 10 | 1 | 1/5 |
| 16% Captisol | B | 10 | 5 | 2 | 2/5 |
| Cosolvent (40% PG:10% EtOH) | I | 2.5 | 1.7 | 1.5 | 3/5 |

Transient local high free concentration of the compound at the injection site was hypothesized to be the main cause of hemolysis. Further experiments in rats to evaluate whether use of Captisol® at varying concentrations, volumes, rate of delivery or addition of buffers could reduce the incidence of hemolysis during bolus administration were unsuccessful.

Example 3

Studies Evaluating the Occurrence of Hemolysis in Rats Upon Bolus Administration of Formulation Containing 22% Solutol Studies were then performed in male and female rats with the aim of reducing the local high concentration of free Compound 1 by 1) incorporating Compound 1 to the hydrophobic core of micelles utilizing Solutol® HS15 (macrogol 15-hydroxystearate, also referred herein as Solutol), 2) injecting via the bolus route Compound 1 incorporated in Solutol and 2) testing for the occurrence of hemolysis (using the Hemastix® reagent strips) at various time intervals (15-60 minutes).

The results indicated that in both male and female rats the occurrence of hemolysis reduced significantly with time (Table 2), and led to the conclusion that local high free concentration of Compound 1 was responsible for the transient hemolysis which occurred within the first few minutes after intravenous dosing.

TABLE 2

Transient Nature of Hemolysis Caused by Compound 1 on Intravenous Administration.

| Dose Group | Time Point | Hemolysis (Male rats) | Hemolysis (Female rats) |
| --- | --- | --- | --- |
| 10 mg/kg | 15 min | 3 | 1 |
|  | 30 min | 0 | 1 |
|  | 60 min | 0 | 0 |
| 20 mg/kg | 15 min | 3 | 3 |
|  | 30 min | 3 | 0 |
|  | 60 min | 0 | 0 |
| 30 mg/kg | 15 min | 3 | 3 |
|  | 30 min | 0 | 2 |
|  | 60 min | 0 | 0 |

Single intravenous 1-2 minute slow-hand bolus using an appropriately sized needle and syringe into tail vein.
Formulation: 10 mg/mL drug, 22% Solutol ® HS15, 20 mM Phosphate buffer, pH 7.0

Example 4

Studies Evaluating the Occurrence of Hemolysis in Rats by Varying the Type of Intravenous Administration To reduce the incidence of hemolysis, a strategy was employed which involved experiments to test if the rate of drug input had an impact on hemolyis. This involved experiments to administer Compound 1 to rats in a micellar solution (HS Solutol® 15) by both the infusion and bolus route. A high rate of incidence of hemolysis was observed in rats when the micellar solution was administered via the bolus route, whereas no hemolysis was observed at the same dose via a 15 minute slow intravenous infusion (Table 3).

TABLE 3

Impact of Infusion Versus Bolus Administration of Compound 1 on Hemolysis.

| Formulation | Bolus (B) or Infusion (I) | Dose (mg/kg) | Dose vol (mL/kg) | Dose Cone (mL/mL) | Incidence + hb-uria/sex |
| --- | --- | --- | --- | --- | --- |
| 7.5% Solutol | I | 25 | 5 | 5 | 0/10 M |
| 7.5% Solutol | B | 25 | 5 | 5 | 5/5 M | infusion = dose administered into tail vein an infusion over 15 minutes

Example 5

Development of Intravenous Microemulsion Formulation of Compound 1 of the Present Invention Materials and Methods Materials for Development of Microemulsion Formulation
Materials used in this study are summarized in Table 4.

TABLE 4

Materials, Composition and Function of Excipients Used in the Microemulsion Formulation of Compound 1

| Materials | Composition | Function |
| --- | --- | --- |
| Compound 1* | 0.2-1.0% | Drug/Active |
| SolutolHS-15 | 0.88-4.84% | Emulsifier |
| Sodium phosphate monobasic | 0.2% | Buffering agent |
| Sodium phosphate dibasic (anhydrous) | 0.284% | Buffering agent |
| NaCl (Brine) | as needed | Tonicity adjuster |
| NaOH | as needed | pH adjuster |
| MIGLYOL ® 812N(MCT*) | 0.2-1.21% | Solubilizer/Hydrophobic component |
| Soybean Oil (LCT*) | 0.12-0.73% | Solubilizer/Hydrobhopic component |

*MCT—medium chain triglyceride;
*LCT—long chain triglycerides
*as the monohydrate hydrochloride salt of the compound of formula I Hemolytic Testing in Rats The methodology for this study was to administer (into the tail vein of a rat) each formulation over 15 minutes by intravenous infusion using an infusion pump or to administer the formulation within two minutes by bolus route using a syringe. Urine was tested for the presence of free hemoglobin using the pooled urine collection method at the six-hour interval. For the six hour pooled urine collection, rats were dosed and placed in a metabolism cage. Six hour post dose, the rats were euthanized by carbon dioxide over-inhalation, and the urine sample was collected. A minimum of five subjects were tested for each formulation and the urine samples were analyzed for hemolysis using Hemastix® reagent strips as indicated in Comparative Example 2.

For the 15 minute and one hour samples, rats were dosed and then returned to their home cage (individually housed) without bedding. If the rat voided any urine in the cage, the urine was analyzed using Hemastix® reagent strips to determine the presence of hemoglobinuria. If the rat did not void in the cage, but voided upon euthanasia, the urine in the euthanasia chamber was analyzed.

Preparation of Dialyzed Solutol in Phosphate Buffered Saline/Distilled Water

Solutol is an amphiphilic molecule and has about 30% of free polyethylene glycol (PEG) in the molecule. The objective of the dialysis study was to minimize/eliminate the hydrophilic portion in the molecule. To get Solutol that is devoid of free PEG, 50 ml of placebo formulation (consisting of 20% Solutol in phosphate buffer) was prepared and filtered through a 0.22 μm filter. The dialysis bag was wet with phosphate buffer at pH 7.0. The weight of the wetted bag was recorded. The dialyzed bag was then filled with 50 ml of the above placebo formulation and this bag was put in no less than 750 ml of phosphate buffer at pH 7.0 and the medium stirred using a stir bar. The buffer outside the dialysis bag was changed two times a day and the process was repeated for a total of 72 hours, with a total of at least 6 exchanges made within 72 hours. After completion of 72 hours, the weight of the dialyzed bag along with the placebo solution inside the bag was recorded. The placebo formulation was also analyzed by HPLC to confirm the levels of PEG in the solution.

Analytical Test Method for Determination of Free Polyethylene Glycol (PEG) Content in Solutol The HPLC conditions for testing of the free PEG in the Solutol molecule is as follows:

Column: Nucleosil CIS Sum 150 × 4.6 mm
Mobile Phase A: 0.025% Phosphoric Acid Solution
Mobile Phase B: Acetonitrile
Column Temp: 30° C.   Sample Temp: 20° C.   Injection Volume: 20 μl
Flow Rate: 1 ml/min   UV Wavelength: 190 nm   Run Time: 60 min
Sample Diluent: Methanol Gradient Program:

| Time (min) | MPA % | MPB % |
|---|---|---|
| 0 | 100 | 0 |
| 40 | 36 | 64 |
| 40.1 | 20 | 80 |
| 50 | 20 | 80 |
| 50.1 | 100 | 0 |

Method of Preparation of Microemulsion Formulation of Compound 1

Below is the process for making the microemulsion composition for Compound 1. A schematic flow diagram for the method of manufacture of the microemulsion formulation is depicted in FIG. 1.

(i) Tear an empty glass beaker.
(ii) Weigh and charge Solutol that has been previously melted in its original container at 65° C. for roughly 15 minutes into the above glass beaker.
(iii) Weigh and charge soybean oil into the above beaker.
(iv) Weigh and charge Miglyol into the above beaker.
(v) Mix the above components well using a stir bar for approximately five minutes.
(vi) Add water for injection to the above beaker after taring the above beaker, to form a microemulsion, followed by Compound 1 and mix.
(vii) The microemulsion formulation is mixed homogenously using a magnetic stir bar for 15 minutes.
(viii) Weigh and charge sodium monobasic and dibasic phosphate to the above formulation.
(ix) Test formulation pH and adjust pH with 1 N NaOH to a pH of 7.5.
(x) Check osmolality of the solution and adjust the tonicity with saturated brine (NaCl) to approx. 290 mM±30 mM.
(xi) Q.S. with water to the final volume of the product.
(xii) Filter the solution through a 0.22 um filter using a Millipore Durapore-GV filter under the laminar flow hood.
(xiii) Aseptically seal the formulation in 10 or 20 ml glass vials for final usage.

Analytical Test Method for Analysis of Samples Containing the Compound of Formula I The HPLC conditions for analysis of Compound 1 are as follows:

Column: Prodigy ODS (3) 150 × 4.6 mm 3 μm
Mobile Phase A: 0.1% Phosphoric Acid Solution
Mobile Phase B: Acetonitrile
Column Temp: 30° C.   Sample Temp: 5° C.   Injection Volumn: 10 μl
Flow Rate: 1 ml/min   UV Wavelength: 215 nm   Run Time: 60 min
Sample Diluent: Methanol Gradient Program:

| Time (min) | MPA % | MPB % |
|---|---|---|
| 0 | 80 | 20 |
| 35 | 20 | 80 |
| 45 | 20 | 80 |
| 45.1 | 80 | 20 |
| 60 | 80 | 20 |

A. Evaluation of Solubility of Compound 1 in Solutol Versus Captisol®

Figure 2:
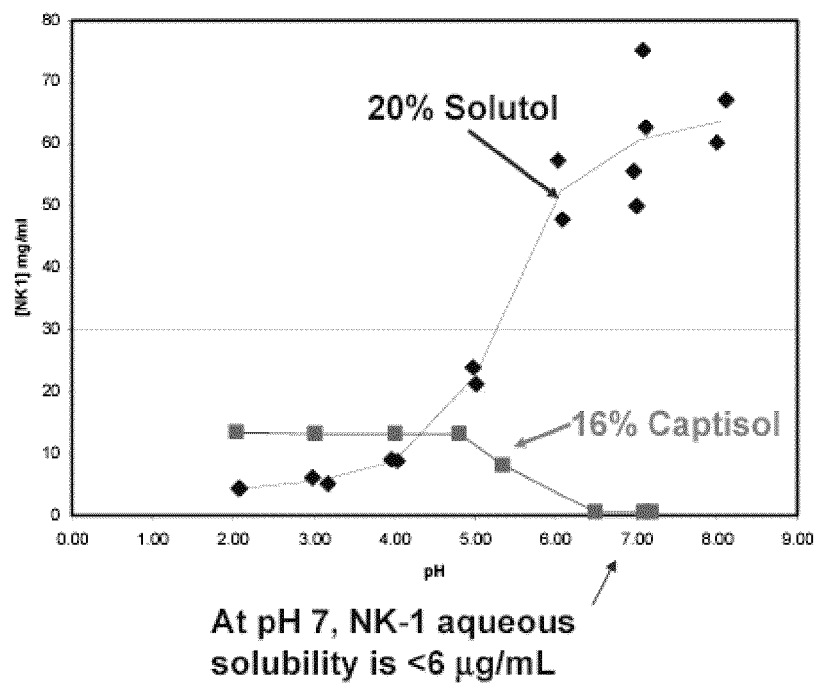
FIG. 2. Equilibrium solubility of Compound 1 in 20% Solutol formulation (diamonds) and 16% Captisol formulation (squares) as a function of pH.

An equilibrium solubility curve of Compound 1 in 20% Solutol was constructed as a function of pH. As shown in FIG. 2, the equilibrium solubility of Compound 1 was substantially higher (~50 mg/ml) in 20% Solutol at a pH of 7.0 compared to <6 μg/ml obtained with the cyclodextrin formulation of 16% Captisol®, that is closer to the aqueous solubility of Compound 1 at pH 7.0. Hence, the enormity of solubility enhancement of Compound 1 was evidently significant from the Solutol micellar formulation compared to the Captisol® based formulation.

B. Evaluation of the Occurrence of Hemolysis in Rats Intravenously Administered Formulation of Solutol Containing Compound 1

A micellar solution with 22% Solutol at 10 mg/ml of Compound 1 at pH 8.0 was used as a starting point for the formulation of Compound 1. A formulation pH of 8.0 was chosen to remain above the pKa of 6.9 of Compound 1, such that Compound 1 would be unionized to reside preferentially in the hydrophobic core of the micelle. However, when the micellar formulation with 22% Solutol was tested in rats, highly unexpected results were obtained in vivo. Severe hemolysis was observed in rats on administering the formulation by a bolus infusion at all dose range tested from 10-30 mg/kg of Compound 1 (Table 5).

TABLE 5

Summary of Bolus Administration of 22% Solutol Formulation of Compound 1 in Rats.

| Dose Group | Red Tinted Urine (observed on animal's fur) | | Red Tinted Plasma (observed after centrifugation) | |
|---|---|---|---|---|
| (mg/kg) | M | F | M | F |
| 10 | 0/3 | 0/3 | 3/3 | 1/3 |
| 20 | 0/3 | 3/3 | 3/3 | 2/3 |
| 30 | 1/3 | 3/3 | 3/3 | 3/3 |

Hemolysis results after single intravenous 1-2 minute slow-hand bolus administration of 22% Solutol HS15, 10 mg/mL drug, 20 mM phosphate buffer formulation using an appropriately sized needle and syringe into tail vein. The above observations were made at 15-60 minutes post dose.

It was hypothesized that the high levels of Solutol may be responsible for the hemolytic activity with the above micellar formulations which were administered as a bolus injection. Solutol is an amphiphilic drug molecule having a lipophilic portion (12-hydroxystearic acid) which constitutes about 70% of the drug molecule and a hydrophilic portion which consists of 30% of free PEG. It was also hypothesized that the presence of the free PEG in the Solutol molecule increases the overall hydrophilicity and facilitates transfer from the lipophilic core to the aqueous phase thereby increasing drug exposure to the red blood cells.

The above hypothesis was tested by reducing the Solutol content in the formulation which would thereby reduce the free PEG content in the molecule. Upon reducing the Solutol concentration the incidence of hemolysis was significantly reduced from as high as 6 out of the 10 rats tested with the 22% Solutol formulation (20 mg/kg dose via infusion) to 0 in 10 rats tested with the 7.5% Solutol formulation at a much higher dose of 25 mg/kg. At 6% Solutol concentration, the incidence of hemolysis was also significantly reduced to 1/10 and 2/10 cases of hemolytic occurrence in two separate studies (Table 6). The incidence of hemolysis observed at the lowest levels of Solutol could be attributed to background incidence and the variability that was observed during rat hemolytic testing.

TABLE 6

Summary of Infusion Administration of Solutol Formulation of Compound 1 in Rats

| Formulation | Dose (mg/kg) | Dose volume (mL/kg)$^a$ | Dose Concentration (mg/mL) | Incidence + hb-uria |
|---|---|---|---|---|
| 6% Solutol | 20 | 7$^b$ | 2.86 | 1/10 |
| 6% Solutol | 20 | 7$^b$ | 2.86 | 2/10 |
| 7.5% Solutol | 5 | 5 | 1 | 0/5 |
| 7.5% Solutol | 25 | 5 | 5 | 0/5 |
|  |  |  |  | 0/5 |
| 15% Solutol) | 25 | 2.5 | 10 | 1/5 |
| 22% Solutol | 20 | 2 | 10 | 8/10 |
| 22% Solutol | 20 | 2 | 10 | 6/10 |

$^a$dose administered into tail vein an infusion over 15 minutes
$^b$volume diluted with 5% dextrose in water (D5W)

To further confirm the above hypothesis, the free PEG was removed from the Solutol molecule by dialysis. Reduction in the free PEG content from 8.5% to 0% reduced the hemolytic occurrence significantly. The incidence of hemolysis was reduced from an occurrence of 10/10 in rats administered 15% Solutol formulation having 8.5% of free PEG to 1 in 10 rats and 2 in 10 rats, respectively, with 6 and 8% of Solutol containing 2% and 0% of free PEG (Table 7).

TABLE 7

Impact of PEG levels on Hemolysis

| Formulation | Dose (mg/kg) | Dose volume (mL/kg)$^a$ | Dose Concentration (mg/mL) | Incidence + hb-uria |
|---|---|---|---|---|
| (8.5% Solutol, 0% PEG) | 20 | 2 | 10 | 2/10 |
| (6% Solutol, ~2% PEG)$^c$ | 20 | 7 | 2.86 | 1/10 |
| (22% Solutol; 7.26% PEG) | 20 | 2 | 10 | 8/10 |
| (15% Solutol; 8.5% PEG) | 20 | 2 | 10 | 10/10$^b$ |

Based on the equilibrium solubility curve, it was determined that 10 mg/ml of Compound 1 may be solubilized at five times lower concentration of the current lead formulation of 22% Solutol that could solubilize 50 mg/ml of Compound 1. Thus, a micellar formulation of 4.4% Solutol (5 times reduced levels from 22% Solutol) at 10 mg/ml of Compound 1, pH 8.0 was chosen as the formulation for all further testing. However, when this formulation at 10 mg/ml of Compound 1 was tested in rats at a dose of 20 mg/kg, the incidence of hemolysis was observed to be still high resulting in 14 occurrences of hemolysis in 20 rats tested in group of two, with 10 rats in each group (Table 8). Repeated testing of the 4.4% Solutol formulation at pH 8.0 produced similar results with 7 out of the 8 subjects having hemolysis (Table 8).

TABLE 8

Hemolysis Results with 4.4% Solutol Intravenous Formulation containing 10 mg/ml of Compound 1

| Formulation | Dose* mg/kg | Volume mL/kg | Conc. mg/mL | pH | % Solutol | % free PEG | Incidence + hb-uria |
|---|---|---|---|---|---|---|---|
| 4.4% Solutol | 20 | 2 | 10 | 8.0 | 4.4 | 1.45 | 7/8 |
| 4.4% Solutol | 20 | 2 | 10 | 7.0 | 22 | 6.6 | 8/10 |
| 4.4% Solutol | 20 | 2 | 10 | 7.0 | 22 | 6.6 | 6/10 |

*Dose as infusion for 15 minutes.

C. Evaluation of the Occurrence of Hemolysis in Rats Intravenously Administered Microemulsion Formulations of Compound 1

Due to the limitation of the micelle by itself to prevent hemolytic occurrence at the higher concentrations, oils were loaded onto the micelles (forming a microemulsion) to shield the drug inside the hydrophobic core and delay the partitioning of Compound 1 to the red blood cells by increasing the overall hydrophobicity of the micelles by inclusion of a triglyceride. It was hypothesized that the inclusion of a triglyceride may also serve to increase the life-time of a micelle which are otherwise highly dynamic structures having a short life-time. The micelles are in equilibrium with the individual surfactant molecules/monomers that undergo constant exchange between the bulk and the micelles, besides the micelles themselves undergoing continuous disintegration and reassembly.

Various short, medium and long chain triglycerides were loaded onto the micelles including capryol, corn oil, soybean oil and MIGLYOL® 812 (also referred herein as Miglyol) to result in a physically stable, microemulsion formulation with a high oil loading. The highest amount of oil at 20% Solutol concentration could be loaded using the medium chain triglyceride, Miglyol. As much as 5% of this medium chain triglyceride could be loaded onto 20% Solutol solution without compromising on the physical stability of the formulation.

Thus, the formulation containing 20% Solutol, 4.4% Miglyol at 10 mg/ml of Compound 1 was tested in rats for hemolysis at a dose of 20 mg/kg Compound 1 by infusion. This formulation did not result in any hemolytic occurrence in the 8 rats tested. The results were similar at the reduced Solutol and MCT concentrations of 4.4% Solutol and 1.1%

Miglyol at 10 mg/ml of Compound 1, resulting in just 1 incidence of hemolysis of the 8 subjects tested (Table 9).

TABLE 9

Hemolysis Testing with Microemulsion (Miglyol-Solutol Based) Formulations of Compound 1.

| Formulation | Dose* mg/kg | Volume mL/kg | Conc. mg/mL | pH | % Composition | % free PEG | Incidence + hb-uria |
|---|---|---|---|---|---|---|---|
| Oil enhanced Solutol | 20 | 2 | 10 | 8.0 | 20% Solutol + 5% Miglyol | 6.6 | 0/8 |
| Oil enhanced Solutol | 20 | 2 | 10 | 8.0 | 4.4% Solutol + 1.1% Miglyol | 1.45 | 1[a]/8 |

[a] represents trace hemolysis in affected animal
*Dose as infusion for 15 minutes.

To confirm the positive results obtained with the oil-enhanced formulation, these formulations were tested again in the rats in a separate study for any occurrence of hemolysis. Surprisingly, the 20% Solutol, 4.4% Miglyol formulation resulted in a high incidence of hemolysis this time, with 4 cases of hemolysis in the 8 subjects tested. The results with the 4.4% Solutol and 1.1% Miglyol were however, comparable to the previous results, producing just one case of hemolysis in the 7 subjects that were administered this formulation (Table 10).

To reduce the hemolytic occurrence observed with the above formulations, these were further modified to include a long chain triglyceride (LCT) to further increase the oil loading in the micelle and result in more pronounced hydrophobicity for enhanced drug retention. Soybean oil, a long chain triglyceride, was used to enhance the oil loading in the Solutol, Miglyol formulation. The maximum amount of soybean oil that could be loaded onto 20% Solutol and 5% Miglyol was approximately 3%. Soybean oil also served to enhance the physical stability of the above formulation possibly via rearrangement of the micellar configuration by inclusion of the long hydrocarbon chain to the medium chain triglyceride, Miglyol, to form a more compact structure.

The results were no different with the 20% Solutol, 4.4% Miglyol and 3% Soybean oil at 10 mg/ml of Compound 1 than a similar formulation without soybean oil. The above formulation resulted in hemolysis in 5 of the 8 rats tested with this formulation. On the contrary, 4.4% Solutol, 1.1% Miglyol and 0.66% soybean oil at 10 mg/ml of Compound 1 yielded absolutely clean results when tested in 8 subjects (Table 10). However, the 20% Solutol, 4.4% Myglyol and 1.5% Vitamin E at 10 mg/ml of Compound 1 did produce hemolytic free results when tested in 8 subjects at a dose of 20 mg/kg by infusion (Table 10).

The conclusions derived from the above studies were (a) lower % of Solutol gives better results, so does lower % of free PEG in the Solutol molecule (b) oil loading results in enhanced drug retention in the micellar core and gives better results in terms of reducing the hemolytic occurrence compared to simple micellar solutions and (c) higher % of Solutol gives more variable results even in the presence of the oils, as was observed with the 20% Solutol with Miglyol alone and with Miglyol and soybean oil combination, compared to the 4.4% Solutol in combination with the above oils. The oil addition clearly improves some high percentage Solutol formulations (e.g. those with vitamin E).

TABLE 10

Hemolysis Testing with Microemulsion Formulations of Compound 1.

| Group | Dose mg/kg | Volume mL/kg | Conc. mg/mL | PH | Incidence + hb-uria |
|---|---|---|---|---|---|
| 4.4% Solutol/1.1% Miglyol | 20 | 2 | 10 | 8.0 | 1[a]/7 |
| 20% Solutol/5% Miglyol | 20 | 2 | 10 | 8.0 | 4[b]/8 |
| Results for comparison from Table 9 | | | | | |
| 4.4% Solutol/1% Miglyol | 20 | 2 | 10 | 8.0 | 1[a]/8 |
| 20% Solutol/5% Miglyol | 20 | 2 | 10 | 8.0 | 0/8 |
| 4.4% Solutol/1.1% Miglyol/0.66% soybean oil | 20 | 2 | 10 | 8.0 | 0/8 |
| 20% Solutol/5% Miglyol/ 3% soybean oil | 20 | 2 | 10 | 8.0 | 5[c]/8 |
| 20% Solutol/5% Miglyol/ 1.5% α-t-tocopherol | 20 | 2 | 10 | 8.0 | 0[c]/8 | severity of affected animals
[a] trace
[b] 3+, 3+, trace, trace
[c] 1+, 3+, 2+, 1+, trace Thus, in order to have a reasonable level of confidence in assuring non-hemolytic results with the oil-enhanced intravenous formulations of Compound 1, three criteria were mapped out to aid in selection of the lead formulation.

(a) To test/re-test reliability (formulation must be able to test clean in >1 study)
(b) To have a consistent performance over batches (formulation must be able to test clean across >1 batch)
(c) Must be robust (formulation must be able to test clean in at least n=10 subjects)

The formulations that were tested based on the above guidelines included 4.4% Solutol, 1.1% Miglyol and 0.66% Soybean oil and 0.88% Solutol, 0.2% Miglyol and 0.12% Soybean oil at 2 mg/ml of Compound 1 at a pH of 8.0. The levels of Solutol were reduced 5-fold in the above case from 4.4% to 0.88% level, to further reduce chances of hemolytic occurrence and obtain reproducible results that were more consistent at the lower levels of Solutol as confirmed by the previous data.

TABLE 11

Hemolytic Testing at Different Sites with Microemulsion
Formulation Containing 4.4% Solutol, 1.1% Miglyol and
0.66% Soybean oil, 2 mg/ml of Compound 1 at pH 8.0.

| Study No. | Dose mg/kg | Infusion minutes | Volume mL/kg | Concentration mg/mL | Incidence + hb-uria |
|---|---|---|---|---|---|
| SN 1 | 20 | 15 | 2 | 10 | 0/8 |
| SN 2 | 20 | 15 | 10 | 2 | 1/7 (1 @ 2+) |
| SN 3 | 10 | 15 | 5 | 2 | 0/10 |
| SN 4 | 10 | 15 | 5 | 2 | 1/20 (1 @ trace) |
| SN 5 | 20 | 15 | 10 | 2 | 1/6 (1 @ 1+) |
| SN 6 | 20 | 15 | 10 | 2 | 0/8 |

The 4.4% Solutol, 1.1% Miglyol and 0.66% Soybean oil at 2 mg/ml of Compound 1 administered by infusion resulted in just three instances of hemolysis of 59 rats tested with this formulation. This study included results obtained (a) from four separate studies conducted at three different sites, (b) performed with at least four different batches and (c) performed in a large number of subjects, as many as 20 rats (n=20) in one such study (Table 11). Thus, the formulation successfully met the above criteria (a-c).

The results were slightly better with the 0.88% Solutol, 0.2% Myglyol and 0.12% Soybean oil formulation with 2 mg/ml of Compound 1 at pH 8.0 resulting in just one instance of hemolysis of 50 rats that received this formulation. These results also included data obtained (a) from three separate studies, (b) performed with three different batches and (c) performed in a large number of rats (n=20) in two such studies (Table 12).

TABLE 12

Hemolytic Testing Conducted at Different Sites With Microemulsion
Formulation Containing 0.88% Solutol, 0.2% Miglyol and 0.12%
Soybean oil, 2 mg/ml Compound 1 at pH 8.0.

| Study No./ | Dose mg/kg | Infusion minutes | Volume mL/kg | Concentration mg/mL | Incidence + hb-uria |
|---|---|---|---|---|---|
| SN1 | 20 | 15 | 10 | 2 | 0/8 |
| SN2 | 20 | 15 | 10 | 2 | 0/2 |
| SN3 | 20 | 15 | 10 | 2 | 1/20 (1@1+) |
| SN4 | 10 | 15 | 5 | 2 | 0/20 |

D. Evaluation of the Occurrence of Hemolysis in Monkeys Intravenously Administered Microemulsion Formulation of Compound 1

Formulations with 1.5%, 3.5% and 5.0% Solutol levels with oils (Solutol:Miglyol:Soybean oil at 6.67:1.67:1) at pH 7.5 (pH 7.5 chosen for chemical stability) formulation as well as reduce the fraction of ionized Compound 1, pKa of 6.9, available to the red blood cells) were tested in 3 monkeys to observe for any occurrence of hemolysis. The 1.5% Solutol formulations lead to hemolysis in one of three monkeys tested. The monkey that tested positive for hemolysis had a +1 rating on a scale of 6 in terms of severity of hemolysis. Similarly, the 2.5% Solutol also lead to one case of hemolysis in 3 monkeys that received this formulation (severity of +2 in the monkey tested positive for hemolysis) (Table 18). However, the 5.0% Solutol gave clean results with no incidence of hemolysis in all the 3 monkeys that were administered this formulation (Table 13).

TABLE 13

Hemolytic Testing with Microemulsion Formulation at 1.5%,
3.5% and 5.0% Solutol with oils (Solutol:Myglyol:Soybean
oil - 6.67:1.67:1), 2 mg/ml Compound 1; pH 7.5 dosed at 20 mg/kg.

| Test Formulation | Dose mg/kg | Infusion minutes | Volume mL/kg | Concentration mg/mL | Incidence + hb-uria |
|---|---|---|---|---|---|
| 1.5% Solutol with oils* | 20 | 15 | 10 | 2 | 1/3 (1@1+) |
| 3.5% Solutol with oils* | 20 | 15 | 10 | 2 | 1/3 (1@2+) |
| 5.0% Solutol with oils* | 20 | 15 | 10 | 2 | 0/3 |

*All the formulations have oil components that include Miglyol and Soybean oil in the following ratio with respect to Solutol (Solutol:Miglyol:Soybean oil - 6.67:1.67:1)

Example 6

Studies with Additional Formulations

Table 14 provides a list of other formulations that were prepared and tested for hemolysis results in addition to the Solutol, co-solvent and cyclodextrin formulations discussed previously.

TABLE 14

| Formulation | Dose mg/kg | Infusion minutes | Volume mL/kg | Concentration mg/mL | Incidence + hb-uria |
|---|---|---|---|---|---|
| Intralipid ® | 5 | 15 | 5 | 1 | 0/2 |
| Emulsion | 5 | 15 | 5 | 1 | 0/4 |
| HSA | 5 | 15 | 5 | 1 | 0/2 |
| Micelle | 5 | 15 | 5 | 1 | 0/5 |
| Micelle | 25 | 15 | 5 | 5 | 0/5 |
| Nanosized | 5 | 15 | 5 | 1 | 0/5 |
| Cremophor RH40 | 20 | 15 | 10 | 2 | 0/12 |
| Cremophor EL | 20 | 15 | 10 | 2 | 1/6 |

In addition, multiple other/identical formulations were prepared and tested as shown below. In each case, the drug Compound 1 was in the form of the HCl monohydrate salt.

Formulation 1:
Compound 1+Cyclodextrin (Captisol);
Delivery Method (Total Daily Dose)(Dose Volume)(Dose Concentration)–hemolysis results:
Bolus (TDD 5 mg/kg)(DV 5 mL/kg)(DC 1 mg/mL)–5/5
Slow Infusion (TDD 10 mg/kg)(DV 10 mL/kg)(1 mg/mL)–1/5

Formulation 2:
Compound 1+cosolvent (PEG/EtOH)
B—
SI(TDD 2.5 mg/kg)(1.5 mL/kg)(1.5 mg/mL)–3/5

Formulation 3:
Compound 1+Polyethylene glycol-660-hydroxystearate, Solutol® HS 15 (22%), 20 mM phosphate buffer; pH 7
Solutol HS 15 forms a micelle
10 mg/mL drug; 10, 20 and 30 mg/kg hemolysis in males; more common at early periods of slow bolus infusion.

Formulation 4:
Bolus or Infusion Dose (mg/kg) Dose vol (mL/kg) Dose Conc. (mg/mL) Incidence+hb-uria/sex

| 7.5% Solutol I | 25 | 5 | 5 | 0/10 M |
| 7.5% Solutol B | 25 | 5 | 5 | 5/5 M |

For the following formulations, the doses were administered into the tail vein of rats via infusion over a 15 minute period. The data for some of the formulations in Table 14 is repeated below in formulations 5-10. The data is shown as dose (mg/kg); dose volume (ml/kg); dose concentration (mg/ml) and hemolysis incidence Formulation 5: 10 ml intralipid (20% soybean oil, 1.2% egg phospholipid, 2.25% glycerol); 100 ul NK-1/ethanol 1 mg/mL; 80 ul 0.1 N NaOH, pH 6.07

| Intralipid (emulsion) | 5 | 5 | 1 | 0/2 |
|---|---|---|---|---|

Formulation 6: (similar to intralipid)

| Emulsion | 5 | 5 | 1 | 0/4 |
|---|---|---|---|---|

Formulation 7: 10 ml HAS (20%); 100 ul NK-1/ethanol solution (1 mg/ml) pH 6.66

| HSA | 5 | 5 | 1 | 0/2 |
|---|---|---|---|---|

Formulation 8: 45 g solutol 15 HS; 15 g propylene glycol, 250 mg NK-1; 8 gr PBS (1×) diluted with 2 gm NK-1 Solutol solution, pH 6.5 or 50 mg/ml drug in Solutol:PG (3:1 w/w) diluted with saline to 1 or 5 mg/ml drug before use.

| Micelle 7.5% Solutol | | | |
|---|---|---|---|
| 5 | 5 | 1 | 0/5 |
| 25 | 5 | 5 | 0/5 |

Micelle = less than 25 nm in diameter

Formulation 9:

| Nanosized | | | |
|---|---|---|---|
| 5 | 5 | 1 | 0/5 |

Formulation 10
22% Solutol; pH 7; phosphate buffer 10 mg/mL hemolysis at slow hand bolus rat tail vein Formulation 11

| 6% Solutol | 20 | 7 | 2.86 | 1/10 |
|---|---|---|---|---|
| | 20 | 7 | 2.86 | 2/10 |

Formulation 12

| 7.5% Solutol | 5 | 5 | 1 | 0/5 |
|---|---|---|---|---|
| | 25 | 5 | 5 | 0/5 |

Formulation 13

| 15% Solutol | 25 | 2.5 | 10 | 1/5 |
|---|---|---|---|---|

11-13-slow infusion in tail vein over 15 minutes

Formulation 14

| 8.5% Solutol; 0% PEG (removed) | | | |
|---|---|---|---|
| 20 | 2 | 10 | 2/10 |

Formulation 15

| 6% Solutol; 2% PEG | | | |
|---|---|---|---|
| 20 | 7 | 2.86 | 1/10 |

Formulation 16*
Oil enhanced micelle (Solutol HS 15+Miglyol H12N (medium chain triglyceride oil)/soybean oil)

The major unsaturated fatty acids in soybean oil triglycerides are 7% alpha-Linolenic acid (C-18:3); 51% linoleic acid (C-18:2); and 23% oleic acid (C-18:1). It also contains the saturated fatty acids 4% stearic acid and 10% palmitic acid.

| 4.4% Solutol (1.45% free PEG)/1.1% Miglyol (pH 8) | | | |
|---|---|---|---|
| 20 | 2 | 10 | 1/8 |
| 20% Solutol (6.6% free PEG)/5% Miglyol (pH 8) | | | |
| 20 | 2 | 10 | 0/8 |

Formulation 17

| 4.4% Solutol/1% Miglyol (pH 8) | | | |
|---|---|---|---|
| 20 | 2 | 10 | 1/7 (1 = trace) |

Formulation 18

| 4.4% solutol/1% Miglyol/.66% soybean oil (pH 8) | | | |
|---|---|---|---|
| 20 | 2 | 10 | 0/8 |

Formulation 19

| 20% Solutol/5% Miglyol (pH 8) | | | |
|---|---|---|---|
| 20 | 2 | 10 | 4/8 (3+, 3+, trace trace) |

Formulation 20

| 20% Solutol/5% Miglyol/3% soy (pH 8) | | | |
|---|---|---|---|
| 20 | 2 | 10 | 5/8 (1+, 2+, 3+, 1+, trace) |

Formulation 21

| 20% Solutol/5% Miglyol/1.5% alphatocopherol (pH 8) | | | |
|---|---|---|---|
| 20 | 2 | 10 | 0/8 |

Formulation 21A

| 4.4% Solutol/1% Miglyol/1.5% alphatocopherol | | | |
|---|---|---|---|
| 20 | 10 | 2 | 2/10 |

Formulation 21B

| 4.4% solutol/1% Miglyol/1.5% α-tocopherol/.6% soybean oil | | | |
|---|---|---|---|
| 20 | 10 | 2 | 0/8 |

Formulation 22

| Compound 1 2 mg/mL .88% Solutol/.2% Miglyol/.12% soy 15 minute infusion | | | |
|---|---|---|---|
| 20 | 10 | 2 | 0/8 |
| 20 | 10 | 2 | 0/2 |
| 20 | 10 | 2 | 1/20 |
| 10 | 5 | 2 | 0/20 |

Formulation 23

| Compound 1 2 mg/mL 4.4% Solutol/1% Miglyol/.6% soy Ph 7.5, 15 minute infusion | | | |
|---|---|---|---|
| 20 | 2 | 10 | 0/8 |
| 20 | 10 | 2 | 1/7 |
| 10 | 5 | 2 | 0/10 |
| 20 | 10 | 2 | 1/6 |
| 10 | 5 | 2 | 1/20 |

Formulations 24-26:
Cremophor RH40 1.25%; Dose-20 mg/kg; Drug conc: ~2 mg/ml; Hemolysis: ~0/8; 15-min infusion
Cremophor EL 1.25%; Dose-20 mg/kg; Drug conc: ~2 mg/ml; Hemolysis: ~1/6; 15 min slow-infusion
Cremophor EL 6%; Dose-20 mg/kg; Drug conc: ~2 mg/ml; Hemolysis: ~4/4; Bolus mode of administration
Formulation 27 (Mixed micelle):
960 µl POPC/ethanol mixture (240 mg POPC)
200 mg Na-glycolic acid
15 mg Compound 1 (HCl-monohydrate)
3 ml PBS (1×)
Target conc: 5 mg/mL
pH: 6.6
Shake-well before dilution. Dilute stock solution with PBS (pH 7.4) to desired conc.
Injection should be completed within 2 h after the dilution.
POPC: palmitic and oleic phosphatidyl choline
Note—this formulation gave high incidence of hemolysis over 15 min slow infusion route at 5 mg/kg; 5 ml/kg and at a dose concentration of 1 mg/mL. Absent any additional information, this formulation is not suitable as an iv formulation at the particular administration route utilized. Longer term infusions might be suitable and or necessary to minimize hemolysis.
Formulation 28
6.7% Solutol and 13.3% Intralipid Drug 2 mg/mL In a preferred embodiment, the formulations of compound 1 are administered by IV Infusion over a 15-30 minute period and would be presented in a bottle having 100 mg/bottle with 50 mL solution having a drug concentration of 2 mg/mL. The dose and volume can be adjusted to provide for additional target doses (e.g. 100 to 200 mg target dose).

One particular advantage of Compound 1 is that it has a half life ($T_{1/2}$) of 180 hrs—this makes it particularly convenient for a one dose per treatment cycle regimen for treating CINV; T1/2 at doses ranging from 5-200 mg as ng/mL of api per time at different doses: The ng/ml at time directly upon administration ranges from 850 ng/mL (200 mg); 430 ng/mL (100 mg); 280 ng/mL (50 mg) with half concentration achieved for all doses at around 180 hrs after administration.

IV formulations can be premixed at 2 mg/mL or can be a concentrate for dilution (10 mg/mL and 20 mg/mL strength for dilution to 2 mg/mL).

The Intralipid® formulation contained 10 ml Intralipid® (20%) (20% Soybean Oil, 1.2% Egg Yolk Phospholipids, 2.25% Glycerin, and Water for Injection); 100 ul Compound 1/ethanol solution (1 mg/ml); 80 ul 0.1 N NaOH to form a pH of 6.07. The intralipid formulation is an emulsion.

The Emulsion formulation (formulation 6) was composed of palmitoyl-oleoyl-phosphotidylcholine (POPC), oleic acid, glycerol and Tween 80.

Micelle particle sizes are typically less than 100 nm and fall within a range of 15 to 100 nm. The Micelle formulation is 45 g Solutol HS; 15 g propylene glycol; 250 mg Compound 1 (as the crystalline monohydrate hydrochloride salt); 8 g PBS (1×) diluted with 2 g Compound 1, Solutol 15S and propylene glycol solution; pH 6.5 to 10 mg/mL; diluted before use or was prepared as 50 mg/mL solution with drug in Solutol:PG (3:1, w:w), diluted with saline to 1 or 5 mg/ml drug before use.

The HSA formulation was 10 ml HSA 20%; 100 ul Compound 1/ethanol solution (1 mg/ml); pH 6.66.

Example 7

Emulsion Formulation Suitable for Bolus and Slow Infusion Administration

Parenteral emulsion formulation based upon medium and long chain triglyercides and with appropriate use of emulsifiers such as egg lecithins and sodium oleate were also formulated. Some of these formulations as recited below resulted in clean results when administered by both the bolus route and by slow infusion. In addition, the emulsions led to reduced hemolysis even at very high doses of 30 mgs/kg. The formulations were subject to microfluidization in which the processing conditions were optimized to result in an emulsion with smaller droplet sizes and a narrow particle size distribution (psd). All formulations processed with an H30Z (200 microns) interaction chamber at 2000 psi achieved sub 500 nm median diameters and $D_{90}$ of less than 600 nm. Certain formulations were also determined to be physically stable after one cycle of sterilization by autoclaving at 121° C. for 20 minutes. Such formulations did not result in any appreciable increase in droplet size after the sterilization process. Thus, a physically stable formulation having Compound 1 (in the form of its crystalline monohydrate hydrochloride salt when formulated) was suitable for bolus and slow infusion intravenous administration and without producing hemolysis in the animals tested.

The emulsion formulations described below have the advantage of enhanced retention of the drug in the hydrophobic core; increased droplet size compared to a micellar formulation to delay drug transfer/partitioning from the oil droplets to the RBCs, and provide increased flexibility in formulating by utilizing naturally occurring lipids as emulsifiers thereby avoiding, for example, free polyethylene glycol which is present in Solutol and which, therefore, further prevents drug transfer from the hydrophobic environment to the RBCs. Parenteral emulsions are used to carry poorly water soluble drugs and typically constitute small oil droplets in an aqueous solution. The preferred emulsifier is selected from those regarded as safe to use for parenteral administration. In the present formulation, lecithin is the preferred emulsifier. Purified egg lecithin is the most preferred. Additional stabilizers can be added including, for example, oleic acid or sodium oleate. Medium chain (Myglyol) and long chain (Soybean oil) triglycerides may also be added. Egg phosphatidyl choline may be used as a stabilizer as well as Lipoid E 80 (77.7% PC, 7.8% PE, 2.5% LPC, 3.0% SPM) (PC=phosphatidylcholine; PE=phosphatidylethanolamine; LPC=lyso-PC; SPM=sphingomyelin) or Lipoid E80S. Glycerin may be used as a tonicity adjustor and ethanol may be used as a co-solvent/solubilizer for the lecithin and drug (Compound of formula I or salt thereof e.g. Compound 1).

The following materials used in this example are summarized in Table 15.

TABLE 15

| Materials | Composition % | Function |
| --- | --- | --- |
| Compound 1* | 0.4-1.5% | Drug/active |
| Egg PC | 3.0% | Emulsifier |
| Lipoid E 80S | 1.2% | Emulsifier |
| Lipoid E80 | 1.2% | Emulsifier |
| Sodium oleate | 0.3% | Emulsifier |
| Glycerin | 2.25% | Stabilizer/co-emulsifier |
| Ethanol | 1.6-4.0% | Cosolvent |
| Myglyol (MCT) | 5-10% | Solubilizer/hydrophobic component |
| Soybean Oil (LCT) | 5-10% | Solubilizer/hydrophobic component |

*compound 1 in the form of solid monohydrate hydrochloride salt
MCT = medium chain triglyceride;
LCT = long chain triglyceride/fatty acid Hemolytic Testing in Animals The methodology for this example was to administer each formulation over 15 minutes by i.v. infusion using an infusion pump or to administer the formulations within 2 minutes by bolus infection using a syringe and delivering the formulation into the tail vein of a rat. Urine was tested by dipstick for the presence of free hemoglobin using the pooled urine collection method at the 6-hour interval. A minimum of four subjects were tested for each formulation and the frequency of hemolysis was observed in such animals.

Preparation of Unprocessed Emulsion Formulation

Figure 3:
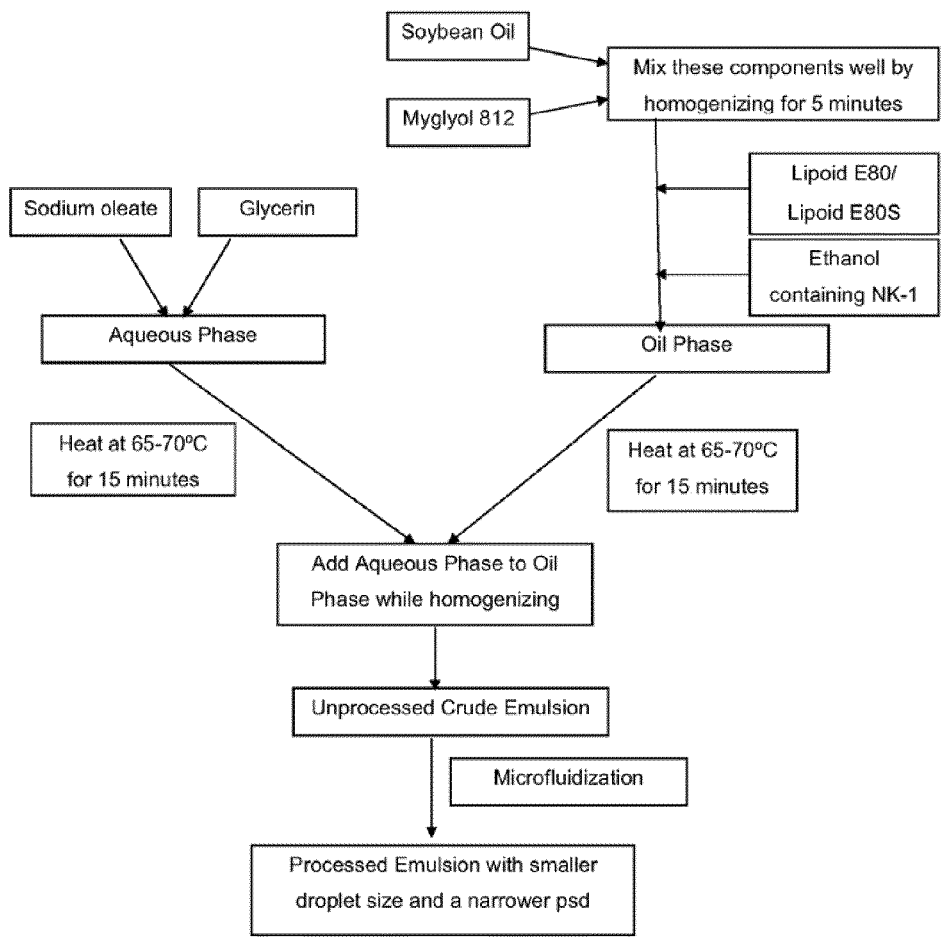
FIG. 3. Schematic Representation of the Method of Manufacture of Emulsion Formulations of Compound 1.

The general procedure for preparing the emulsion was as follows (FIG. 3):

(1) Weigh out the required amount of Myglyol and Soybean oil into the beaker;
(2) Homogenize the above pre-mix for 5 minutes to blend and mix the two components;
(3) Add the required amount of Lipoid. E80®/Lipoid E80S into the above beaker;
(4) Add the required amount of ethanol containing 200-250 mcg/ml of Compound 1 as the monohydrate hydrochloride salt;
(5) Weigh out the required amount of sterile water in a separate beaker;
(6) Add the specified quantity of glycerin to the aqueous phase and mix it for 2-3 minutes;
(7) Add the specified quantity of sodium oleate to the aqueous phase, if present in the formula;
(8) Heat the oil phase and the water phase separately at about 65-70° C. for 15-20 minutes;
(9) Add the aqueous phase to the oil phase, q.s. to final volume with sterilized water and homogenize the dispersion for approximately 1-2 minutes;
(10) Cool the dispersion to room temperature before filling a vial.

Preparation of Processed Emulsion Formulations Using Microfluidization

The unprocessed emulsion described above or within the scope of the invention may be subsequently passed through a microfluidizer to result in more stable emulsions with a narrow droplet size distribution. A microfluidization process involves the use of a microfluidizer that is designed to supply a desired pressure to the product at a constant rate to the product stream. As a result the product stream accelerates to high velocities through precisely designed fixed geometry microchannels (interaction chamber), creating shear rates within the product stream that are much higher than any other conventional methods. This causes the droplets to break down into smaller sizes and results in a formulation with a more uniform and narrow droplet size distribution for enhanced physical stability.

Procedure for Processing/Characterization of Formulations Using Microfluidizer

Colloidal emulsions were processed using either F20Y (75 micron) interaction chamber with a pressure range between 4,100 and 10,000 psi or H30Z (200 microns) at a pressure of 2000 and 5000 psi. The number of passes ranged from one to three. A water-bath enclosing the interaction chamber was used to prevent any temperature increase for the product during the microfluization step Analysis involved the use of an optical microscope and a particle size analyzer. Images were captured for each sample collected after processing. Particle size analysis was measured for the unprocessed sample and at the conclusion of each cycle of microfluidization.

Steam Sterilization

The formulations were filled and sealed in a glass vial and put in an autoclave for terminal sterilization at one cycle of 121° C. for 20 minutes. The particle size was measured using the Malvern Zetasizer Nano-ZS to observe changes in droplet size distribution after the sterilization process. The instrument operates on the principle of dynamic light scattering.

Formulations and Results

Two emulsion formulations were formulated with Egg PC and a combination of medium and long chain triglycerides. The emulsion formulation produced non-hemolytic results on both infusion and bolus administration in 4 and 6 rats respectively (Table 16). However, these particular formulations were not stable beyond a 24 hour period unless shaken to impart shear for adequate dispersion.

TABLE 16

| Batch No. | Formulation composition | Drug concentration mg/ml | Target Dose (mg/kg) | Dose Route | Time Point | Hemoglobinuria |
|---|---|---|---|---|---|---|
| 85266 MCT-LCTinf | Soybean oil-5% Myglyol 5% Egg PC-1.2% Ethanol 2% | 10 | 20 | Iv infusion | 6 | 0/4 |
| 85266 MCT-LCTbol | Soybean oil-5% Myglyol 5% Egg PC-3.0% Ethanol 2% | 10 | 20 | Iv bolus | 6 | 0/6 |

The emulsion formulations for further testing in rats were formulated at 20% w/w of oil load and made physically stable using Lipoid E80S as the emulsifier. High oil content was desirable in order to retain compound 1 in the hydrophobic core. Lipoid E80S has a high phosphotidyethanolamine (PE) content and acts an as anionic emulsifier. This product is commercially available from Lipoid KG of Ludwigshafen, Germany. The PE content in Lipoid E80S is about 20% while egg phosphotidylcholine constitutes about 80% of the substance. These formulations were tested at a dose of 20 mg/kg of compound 1 by both bolus and infusion. The incidence of hemolysis was high at this oil load as can be seen in Table 17.

TABLE 17

| Batch No. | Formulation composition | Drug Conc (mg/ml) | Target Dose (mg/kg) | Dose Route | Time Point (hr) | Hemoglobinurea |
|---|---|---|---|---|---|---|
| 85266-M/L20% inf | Soybean oil-10% Myglyol-10% Lipoid E80S-1.2% Glyerin-2.25% Ethanol-1.6% | 4 | 20 | i.v. infusion | 6 | 3/6 |
| 85266-M/L20% | Soybean oil-10% Myglyol-10% Lipoid E80S-1.2% Glyerin-2.25% Ethanol-4.0% | 10 | 20 | i.v. bolus | 6 | 4/6 |

Reducing the oil load from 20% to 10% in the formulation produced clean hemolysis results in both the bolus route and in the slow infusion route (Table 18).

TABLE 18

| Batch No | Formulation composition | Drug Con (mg/ml) | Target Dose (mg/kg) | Dose Route | Time Point (hr) | hemoglobinuria |
|---|---|---|---|---|---|---|
| 85266 M/L10% inf | Soybean oil-5% Myglyol-5% Lipoid E80S-1.2% Glyerin-2.25% Ethanol-1.6% | 4 | 20 | i.v. infusion | 6 | 0/6 |
| 85266-M/L10% | Soybean oil-5% Myglyol-5% Lipoid | 10 | 20 | i.v. bolus | 6 | 0/6 |

TABLE 18-continued

| Batch No | Formulation composition | Drug Con (mg/ml) | Target Dose (mg/kg) | Dose Route | Time Point (hr) | hemoglobinuria |
|---|---|---|---|---|---|---|
| | E80S-1.2% Glyerin-2.25% Ethanol-4.0% | | | | | |

The preferred emulsion formulation thus contained a 10% oil load. Sodium oleate was added as an additional ingredient but did not produce favorable hemolytic results in all delivery routes (Table 19).

TABLE 19

| Batch No. | Formulation composition | Drug conc. (mg/ml) | Target Dose (mg/kg) | Dose Route | Time Point (hr) | Hemoglobinuria |
|---|---|---|---|---|---|---|
| 85266-M/L 10% SOinf | Soybean oil-5% Myglyol-5% Lipoid E80*-1.2% Sodium oleate 0.3% Glyerin-2.25% Ethanol-1.6% | 4 | 20 | i.v. infusion | 6 | 1/5 |
| 85266-M/L 10% SObol | Soybean oil-5% Myglyol-5% Lipoid E80-1.2% Sodium oleate 0.3% Glyerin-2.25% Ethanol-4.0% | 4 | 8 | i.v. bolus | 6 | 2/5 |

Lipoid E80 has a 10% PE content as compared to 20% in Lipoid E80S.

The formulations without sodium oleate and with a higher concentration of drug load (30 mg/kg) were also tested (Table 20).

TABLE 20

| Batch No | Formulation composition | Drug Conc (mg/ml) | Target Dose (mg/kg) | Dose Route | Time Point (hr) | hemoglobinuria |
|---|---|---|---|---|---|---|
| 85266 M/L 10% inf2 | Soybean oil-5% Myglyol-5% Lipoid E80-1.2% Glyerin-2.25% Ethanol-2.0% | 5 | 30 | Iv infusion | 6 | 1/5 |
| 85266 M/L 10% bol3 | Soybean oil-5% Myglyol-5% Lipoid E80-1.2% Glyerin-2.25% Ethanol-4.0% | 15 | 30 | Iv bolus | 6 | 1/5 |

Five emulsion formulations listed below were processed using the microfluidization technique. The final particle size ($D_{10}$, $D_{50}$ and $D_{90}$) obtained after processing these formulations along with the number of passes involved, the pressure used to force the liquid through the interaction chamber and the type of interaction chamber used is tabulated in Table 21.

TABLE 21

| Sample | Interaction chambers | Pressure (psi) | Passes | D10 (nm) | D50 (nm) | D90 (nm) |
|---|---|---|---|---|---|---|
| INFWSO | Unprocessed | 0 | 0 | 1365 | 2643 | 4868 |
| INFWSO | F20Y | 10,000 | 1 | 198 | 316 | 4205 |
| INFWSO | F20Y | 4,100 | 1 | 237 | 390 | 728 |
| INFWSO | F20Y | 4,100 | 2 | 228 | 334 | 461 |
| INFWSO | F20Y | 4,100 | 3 | 217 | 318 | 437 |
| INFWSO | H30Z | 2,000 | 1 | 352 | 914 | 2862 |
| INFWSO | H30Z | 2,000 | 2 | 323 | 566 | 992 |
| INFWSO | H30Z | 2,000 | 3 | 309 | 442 | 578 |
| INFSO | Unprocessed | 0 | 0 | 1949 | 4911 | 15,186 |
| INFSO | H30Z | 2,000 | 1 | 474 | 699 | 972 |
| INFSO | H30Z | 2,000 | 2 | 358 | 501 | 655 |
| INFSO | H30Z | 2,000 | 3 | 335 | 464 | 608 |
| INFSO | H30Z | 5,000 | 1 | 344 | 544 | 818 |
| INFSO | H30Z | 5,000 | 2 | 272 | 386 | 503 |
| INFSO | H30Z | 5,000 | 3 | 231 | 327 | 433 |
| BOL10WSO | Unprocessed | 0 | 0 | 1967 | 3892 | 6,873 |
| BOL10WSO | H30Z | 2,000 | 1 | 313 | 597 | 1,119 |
| BOL10WSO | H30Z | 2,000 | 2 | 308 | 498 | 735 |
| BOL10WSO | H30Z | 2,000 | 3 | 276 | 422 | 595 |
| BOL10WSO | H30Z | 5,000 | 1 | 266 | 529 | 3192 |
| BOL10WSO | H30Z | 5,000 | 3 | 227 | 341 | 482 |
| BOL10SO | Unprocessed | 0 | 0 | 885 | 2,028 | 3,868 |
| BOL10SO | H30Z | 2,000 | 1 | 284 | 507 | 905 |
| SOL10SO | H30Z | 2,000 | 2 | 299 | 461 | 661 |
| BOL10SO | H30Z | 2,000 | 3 | 259 | 370 | 493 |
| BOL10SO | H30Z | 5,000 | 1 | 262 | 479 | 1,186 |
| BOL10SO | H30Z | 5,000 | 2 | 235 | 365 | 541 |
| BOL10SO | H30Z | 5,000 | 3 | 213 | 312 | 431 |
| BOL15SO | Unprocessed | 0 | 0 | 1,383 | 4,505 | 10,745 |
| BOL15SO | H30Z | 2,000 | 1 | 345 | 652 | 1,259 |
| BOL15SO | H30Z | 2,000 | 2 | 289 | 470 | 720 |
| BOL15SO | H30Z | 2,000 | 3 | 273 | 410 | 569 |

INFWSO is the same formulation composition as Batch No.: 85266-M/L10% inf
INFSO has the same formulation composition as Batch No.: 85266-M/L10% SOinf
BOL10WSO has the same formulation composition as Batch No.: 85266-M/L10%
BOL10SO has the same formulation composition as Batch No.: 85266-M/L10% SObol
BOL15SO has the same formulation composition as Batch NO.: 85266-M/L10% bol3

Figure 4:
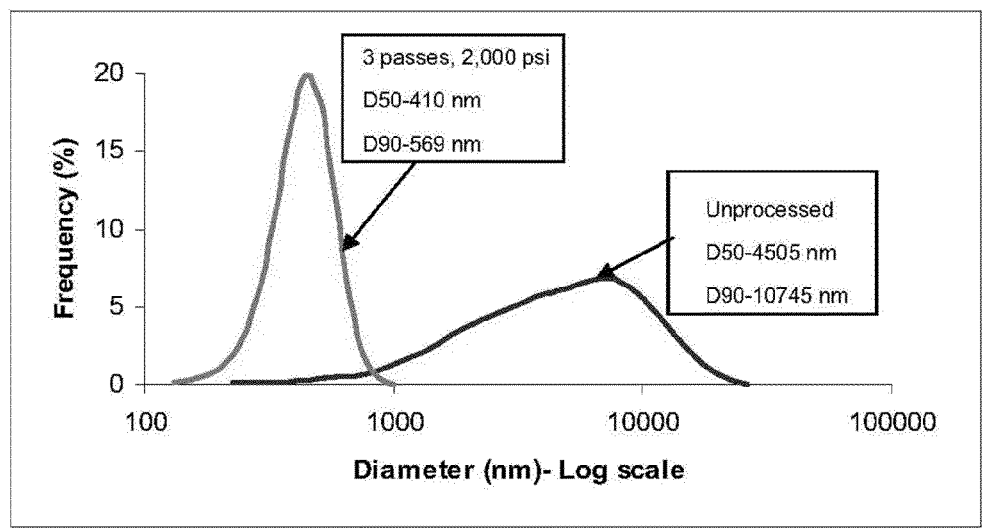
FIG. 4. Particle Size Distribution of the Unprocessed Formulation, BOL15SO and Processed Formulation involving 3 passes at 2000 psi using the H30Z Interaction Chamber.

A narrower and more uniform particle size distribution (psd) was obtained for all the processed formulations. As can be seen in FIG. 4, the psd curve for BOL15SO shifted significantly to the left after microfluidization compared to the unprocessed formulation subjected to three passes at a pressure of 2,000 psi. The $D_{50}$ and $D_{90}$ values for the unprocessed BOL15SO were 4.505 um and 10.745 um respectively, and shifted to 410 nm and 569 nm respectively, after passing the formulation through three passes using a H30Z (200 micron) interaction chamber at 2000 psi pressure. The microscopic images confirm the uniformity in the psd of the oil droplets obtained after subjecting the formulation to 3 passes of microfluidization at 2000 psi compared to one pass at 2000 psi (FIG. 7).

Figure 7:
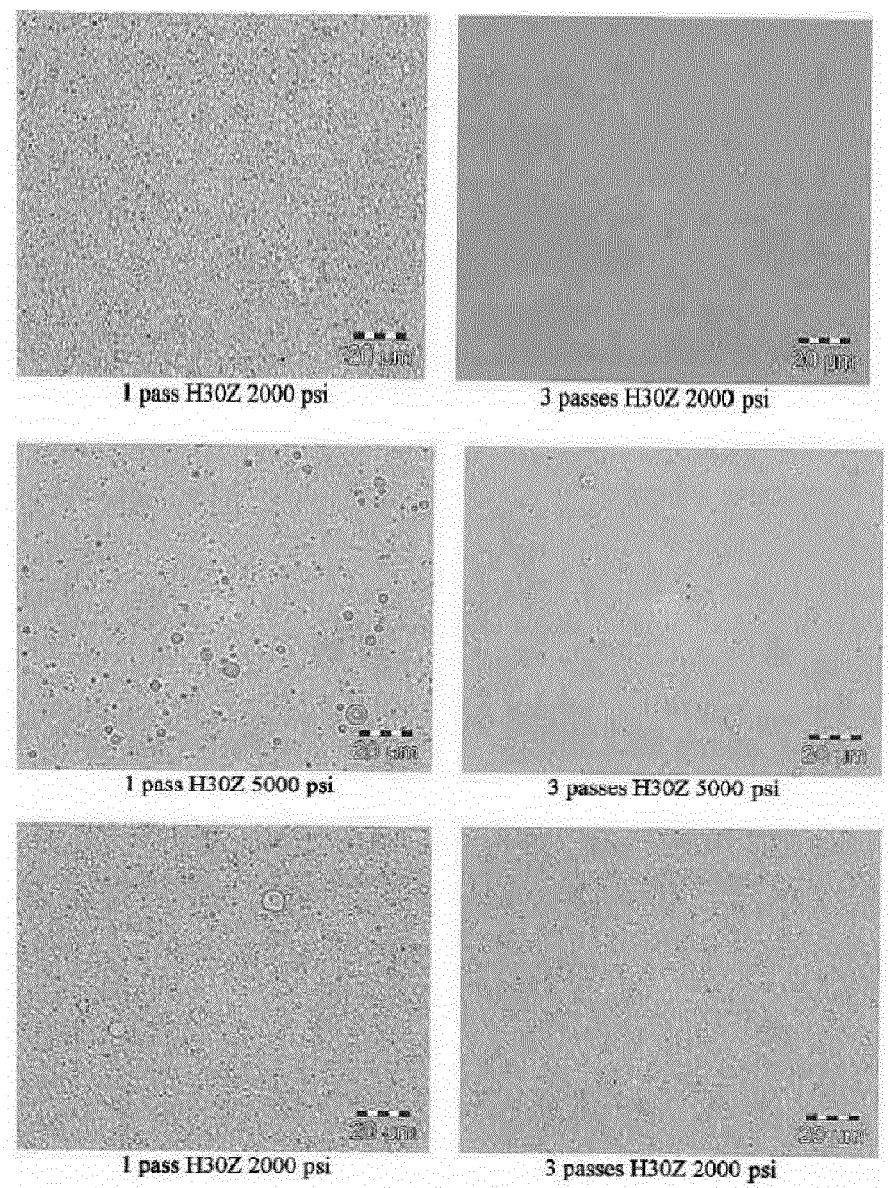
FIG. 7. Optical microscopic images of formulations BOL 15SO and INFWSO during microfluidization.

FIG. 7 shows the Optical microscopic images of formulations, BOL15SO and INFWSO during microfluidization. The optical microscopy results clearly show the impact of number of cycles of microfluidization on the formulation, BOL 15SO (top 2 images) and INFWSO (bottom 4 images). The images on the right hand side are observed to be devoid of very large oil globules with a more uniform and a narrow size distribution.

Figure 5:
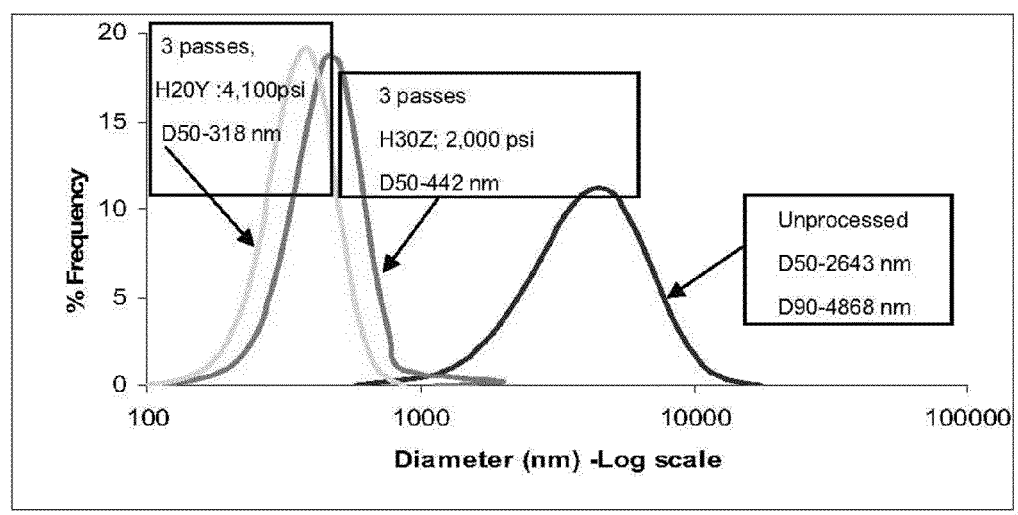
FIG. 5. Particle size distribution of the Unprocessed Formulation INFWSO and Processed formulation involving 3 passes at 2000 psi using the H30Z interaction chamber and 4,100 psi using H20Y Interaction Chamber.

A similar observation was made with respect to INFWSO. The $D_{50}$ and $D_{90}$ values changed from 2.643 um and 4.848 um for the unprocessed formulation to 442 nm and 578 nm with three passes at 2,000 psi using the H30Z interaction chamber. The psd curve shifted further to the left and the $D_{50}$ and $D_{90}$ values were recorded at 318 and 437 nm respectively using the F20Y interaction chamber with micropore channels of 75 microns after subjecting the formulation to 3 passes at a pressure of 4,100 psi (FIG. 5). Microscopy images of the processed formulation after one pass at 2000 and 4,100 psi show large oil globules and a non uniform psd which clearly became more uniform after subjecting the formulation to more passes (FIG. 7).

Figure 6:
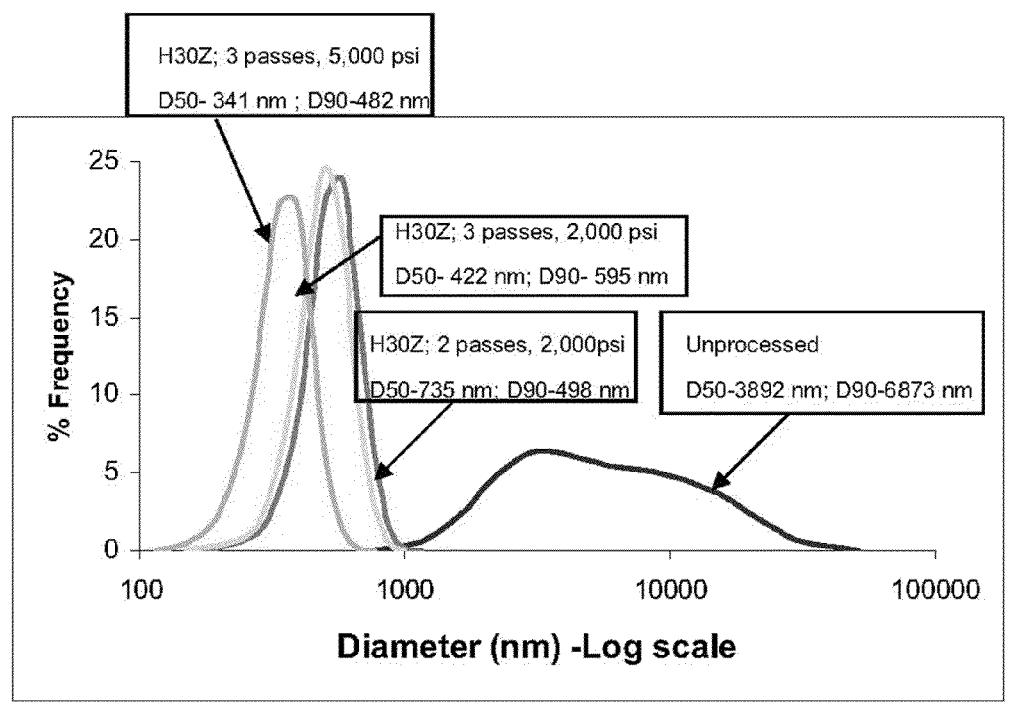
FIG. 6. Particle size distribution of the Unprocessed Formulation BOL10WS and the Processed Formulation involving 2 and 3 passes of the formulation using the H30Z interaction chamber at 2000 psi and 4,100 psi.

BOL10WSO yielded similar results on processing with the curve for the psd of oil droplets shifting significantly to the left after microfluidization. The $D_{50}$ and $D_{90}$ values were recorded at 422 um and 595 um using H30Z interaction chamber on processing these emulsions at a pressure of 2,000 psi after three cycles compared to the unprocessed formulations which had a $D_{50}$ and $D_{90}$ of 3.892 um and 6.873 um. Use of higher pressure of 5,000 psi using the same interaction chamber at three passes, further shifted the curve to the left yielding $D_{50}$ and $D_{90}$ values of 341 nm and 482 nm respectively (FIG. 6). The effect of the microfluidization on the number of cycles and the smaller oil droplets obtained after subjecting the formulation to a higher pressure was observed clearly in the microscopic images (FIG. 8).

Figure 8:
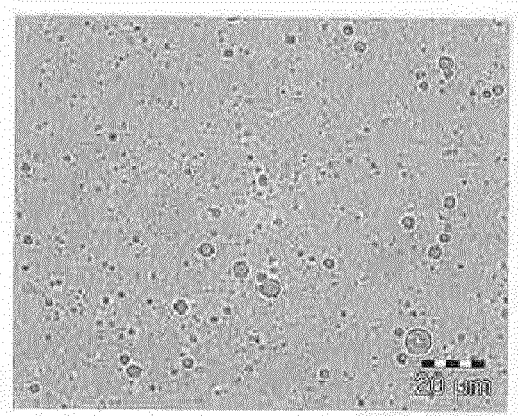
FIG. 8. Optical Microscopic images of formulations BOL 10WSO during microfluidization.
Figure 8:
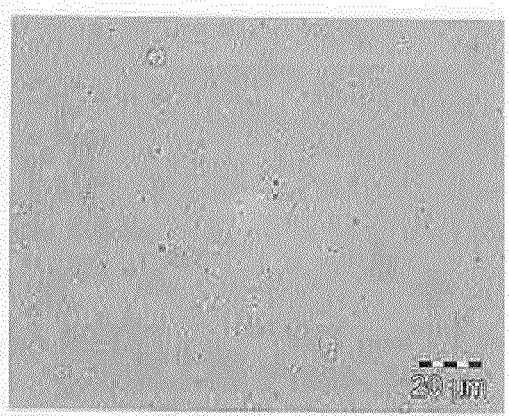
Figure 8:
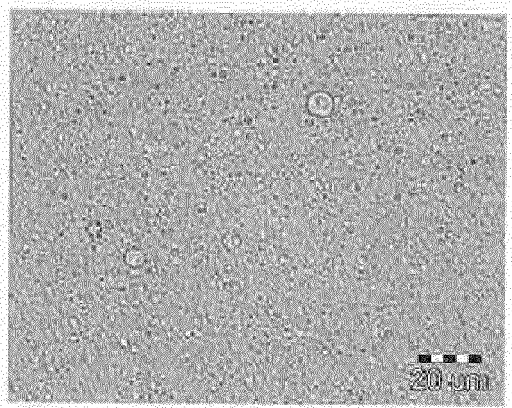
Figure 8:
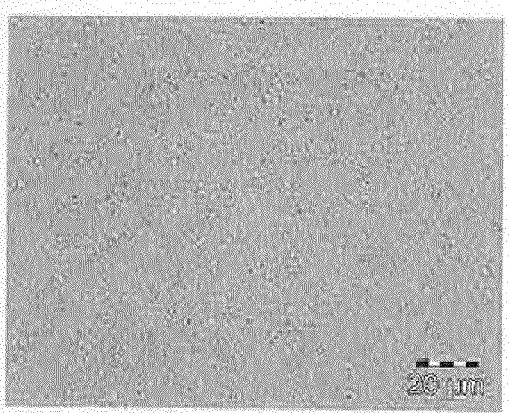

FIG. 8 shows Optical microscopic images of formulations, BOL10WSO during microfluidization.

The optical microscopy results clearly show the impact of the pressure and the number of
cycles of microfluidization on formulation, BOL10WSO. The images on the right hand side are observed to be devoid of very large oil globules with a more uniform and narrow size distribution. Further, the oil droplets are also smaller when the formulation is subject to microfluidization at higher pressure as expected.

Figure 9:
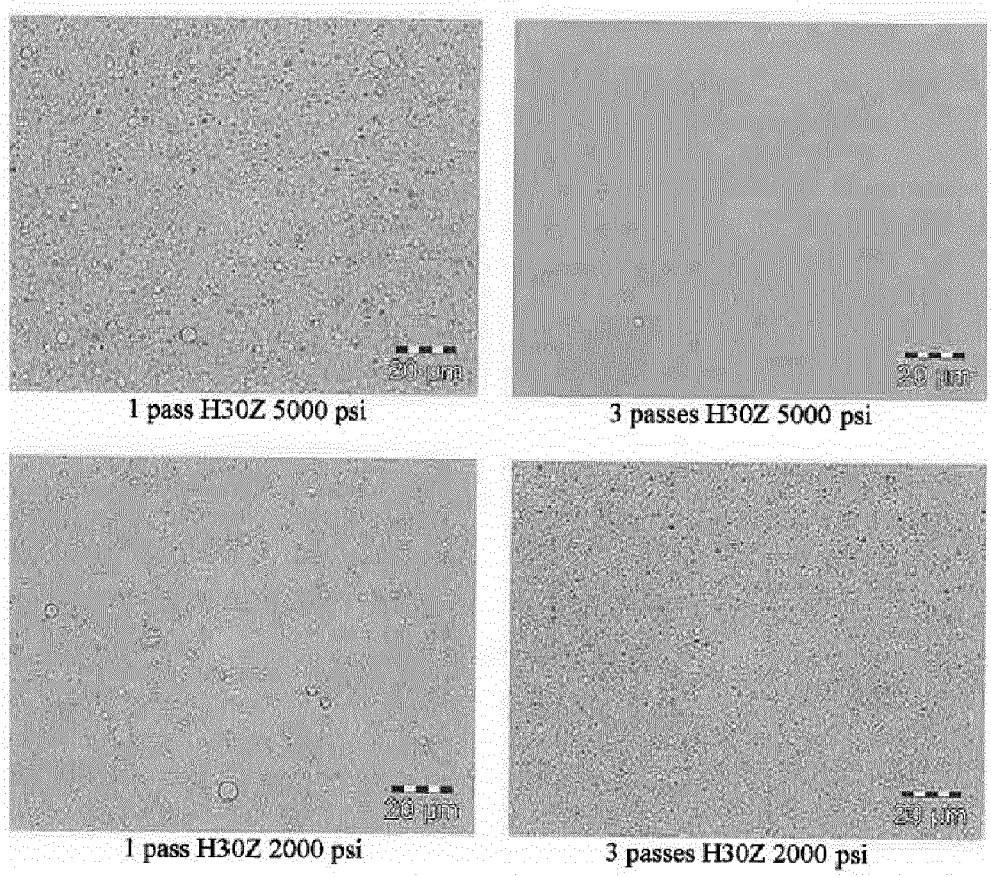
FIG. 9. Optical Microscopic images of formulations INFSO during microfluidization FIG. 10. Optical Microscopic images of formulations BOL 10SO during microfluidization FIG. 11. PSD curve for INFWSO after sterilization.
Figure 10:
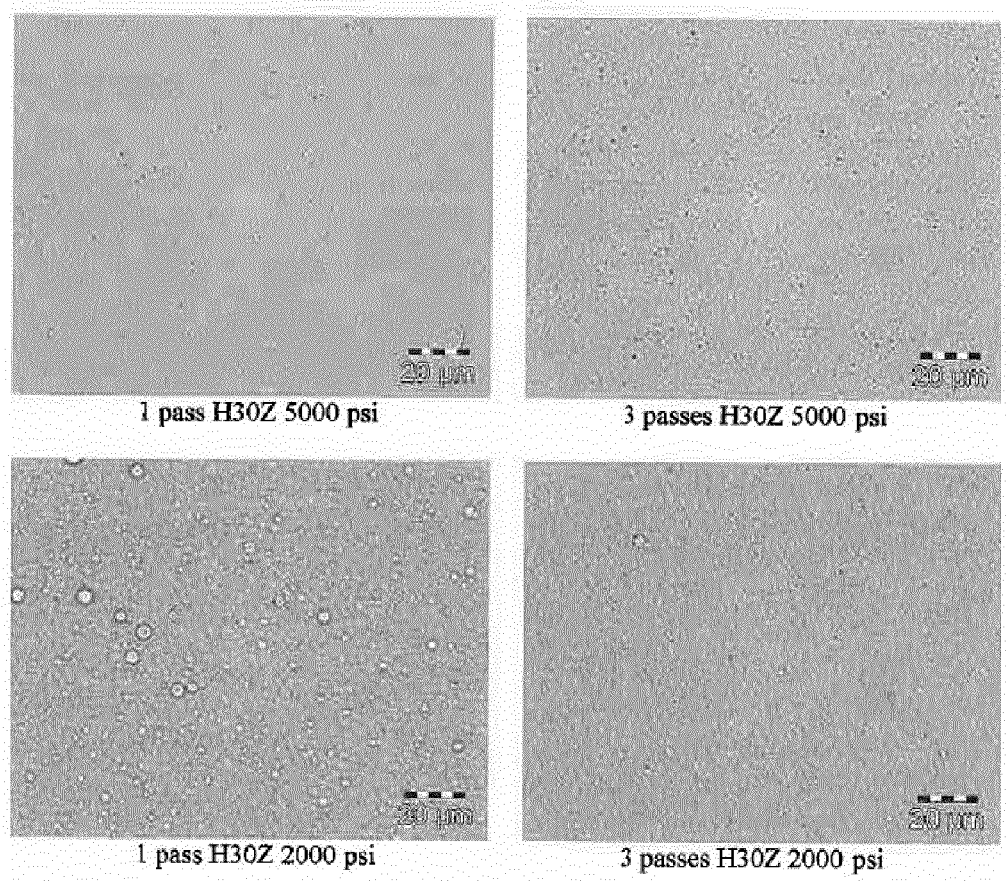

Similar observations were seen with the formulations INFSO and BOL10SO (FIGS. 9 and 10). FIG. 9 shows Optical microscopic images of formulations, BOL15SO and INFWSO during microfluidization. The optical microscopy results clearly show the impact of the number of cycles of microfluidization on formulation, INFSO. Higher number of cycles results in a more uniform particle size distribution. FIG. 10 shows Optical microscopic images of formulations, BOL10SO during microfluidization.

The optical microscopy results clearly show the impact of the number of cycles of microfluidization on formulation, BOL10SO. Higher number of cycles results in a more uniform particle size distribution.

Figure 11:
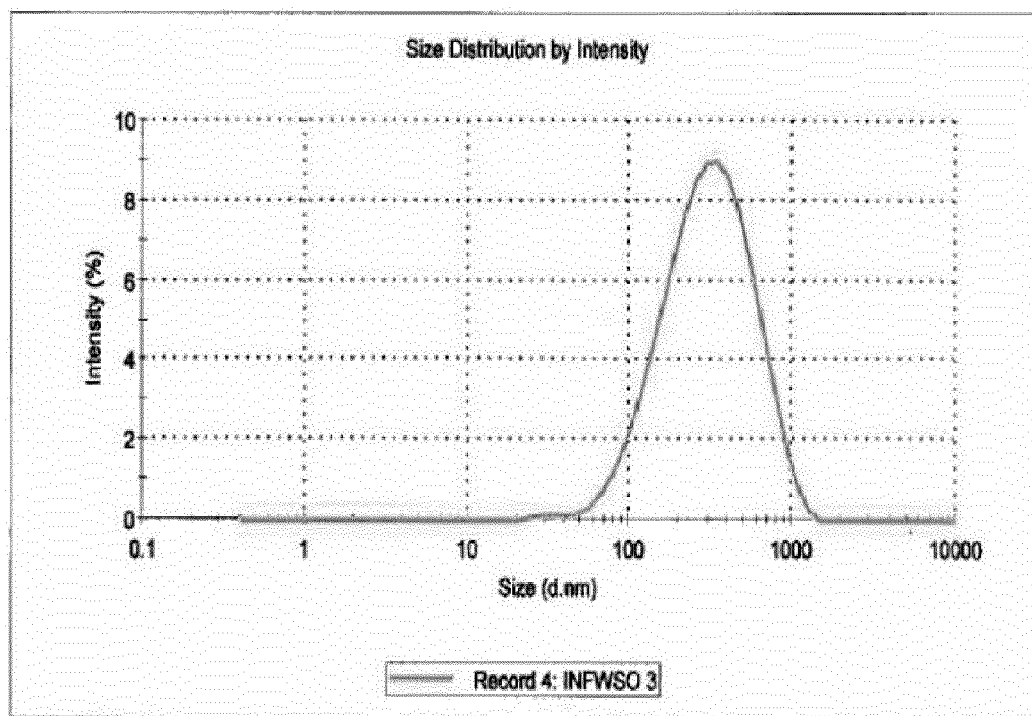
Figure 12:
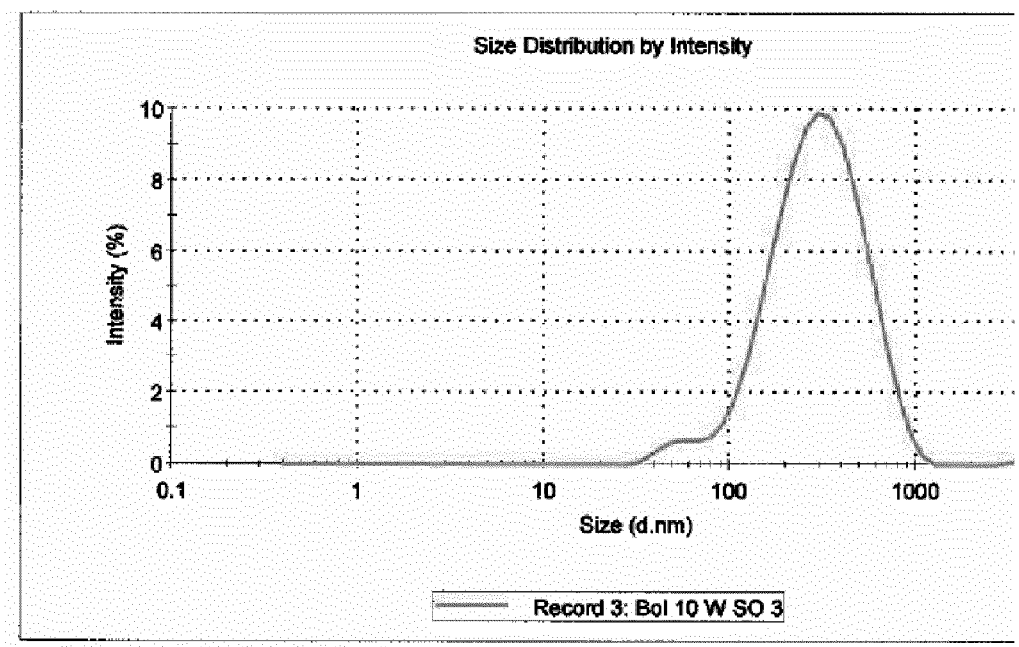
FIG. 12. PSD curve for BOL 10WSO after sterilization.
Figure 13:
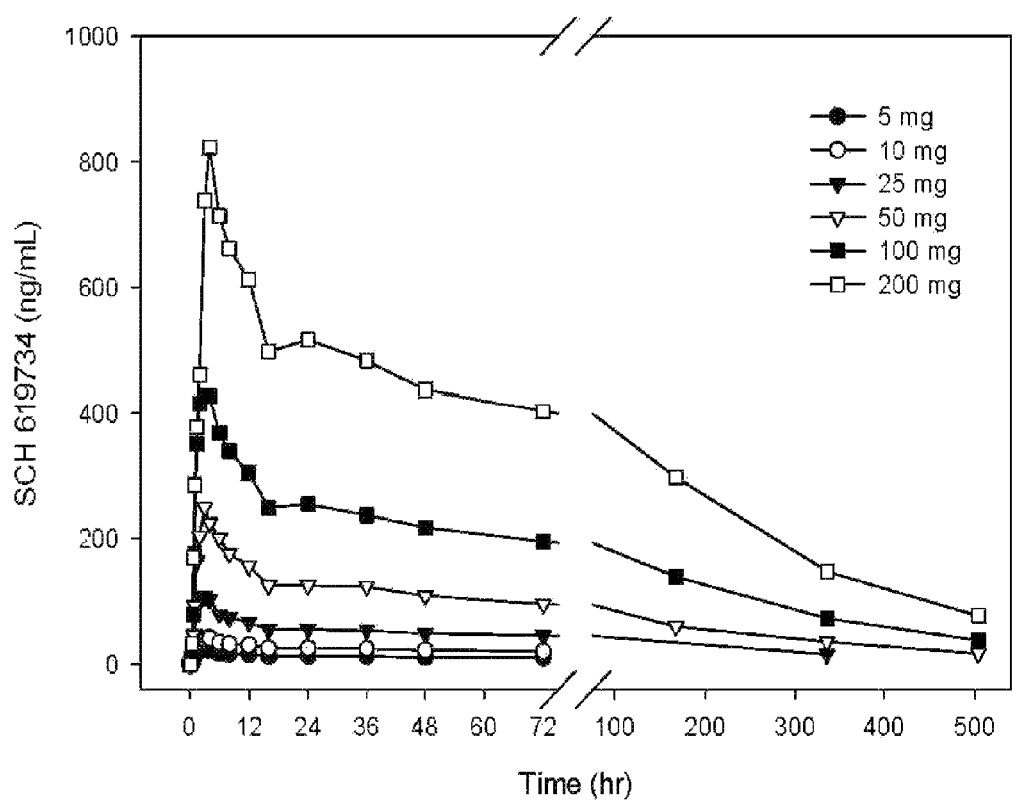
FIG. 13. ng/ml blood levels of Compound 1 administered by intravenous administration at various doses.

Microfluidization processing thus provided physically stable emulsion formulations comprising a compound of Formula I and pharmaceutically acceptable salts thereof. The present invention also relates to emulsion formulations of Formula I and salts thereof having droplets with median diameters of about 500 nm or less and a $D_{90}$ of about 600 or less. Even smaller droplet particle sizes were achieved when the formulations were subject to additional passes and higher pressures. The formulations were then subjected to autoclaving to sterilize the formulations for intravenous administration. No visible stability issues arose as a result of the autoclaving. INFWSO and BOL10WSO were autoclaved and after visual inspection the mean particle size obtained after one cycle was determined to be 353.4 nm and 336.7 nm respectively (FIGS. 11 and 12). Thus, non-hemolytic results were reproducibly achieved using phospholipid based emulsion formulations for both bolus and slow infusion administration.

As indicated above, the formulations are useful in the prevention and treatment of nausea and vomiting associated with radiation therapy for cancer treatment; chemotherapy therapy for cancer treatment and with post operative associated nausea and vomiting. The course of therapy comprises a single dose of the formulation comprising a compound of Formula I or salt thereof on day one before the initiation of chemotherapy followed by once a day dosing on days two and three. The course of therapy also comprises a single dose administration on day 1. The iv solution can be in the form of a 2 mg/ml solution with 50 mls necessary to deliver 100 mgs to the patient in need of treatment thereof. The formulation can be a ready to go premixed solution or a concentrate which can be dilute before use. The lyophilized formulations disclosed herein may be in the form of a powder which is mixed with saline or appropriate buffer solution before use.

Example 8

Prodrugs

Two prodrugs shown below were prepared by reacting the activated carbonyl compound with a compound of formula I. The glucamine phosphate salt shown below gave clean hemolysis results in a Dextrose water solution without any solubilizer as measured at two different time points and in both urine and plasma.
Prodrugs:

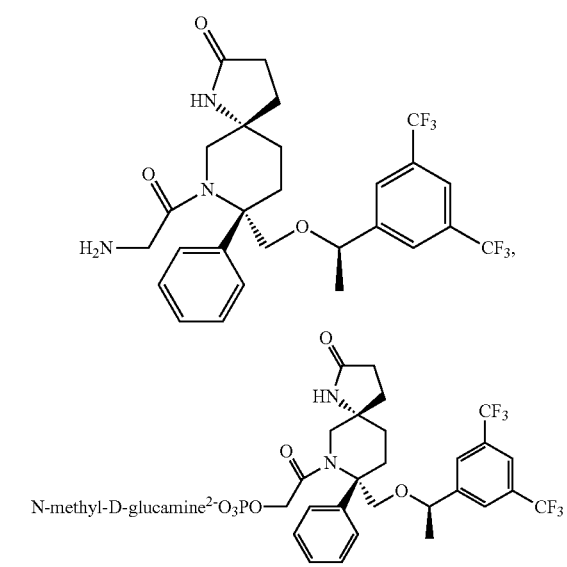

Hemolysis Data for Glucamine Phosphate Salt Prodrug in Dextrose/water:

| 20 mg/kg dose | 2 mL/kg | 10 mg/mL | 0/4 urine; 1/4 plasma .25 hour timepoint |
| 20 | 2 | 10 | 0/3 urine; 0/3 plasma 1 hr timepoint |

Data for amine generated with a vehicle (10% Solutol) 0.25 hr 3/3 hemolysis.

What is claimed:

1. A method for treating nausea and/or emesis in a patient in need of treatment, the method comprising intravenously administering to the patient an effective amount of a pharmaceutical composition comprising:

a) a compound of Formula I

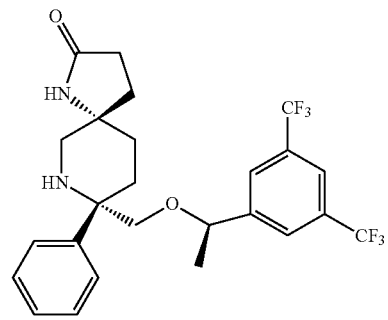 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
b) macrogol 15-hydroxystearate in an amount of from about 0.50% to about 10.0% by weight of the total composition;
c) a medium chain triglyceride in an amount of from about 0.10% to about 2.5% by weight of the total composition;
d) a long chain triglyceride in an amount of from about 0.10% to about 1.5% by weight of the total composition; and
e) at least one buffer, wherein the weight ratio of macrogol 15-hydroxystearate:medium chain triglyceride:long chain triglyceride in the composition is about 5-100:1-5:1, and wherein the pH of the composition is from about 6.5 to about 8.0; and
with incidence of hemolysis that is below 20% when administered across a population.

2. The method of claim 1, wherein said pharmaceutical composition comprises:

(a) a compound of Formula I

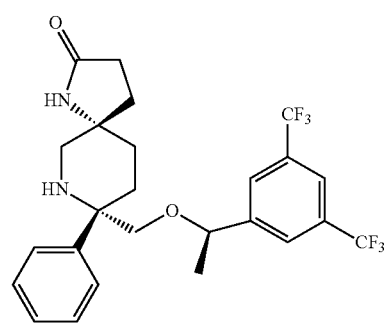 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
(b) macrogol 15-hydroxystearate in an amount of about 4.4% by weight of the total composition;
(c) at least one medium chain triglyceride in an amount of about 1.1% by weight of the total composition;
(d) refined soybean oil in an amount of about 0.66% by weight of the total composition; and
(e) a phosphate buffer, wherein the pH of the composition is about 7.5.

3. The method of claim 1, wherein said pharmaceutical composition comprises:

(a) a compound of Formula I

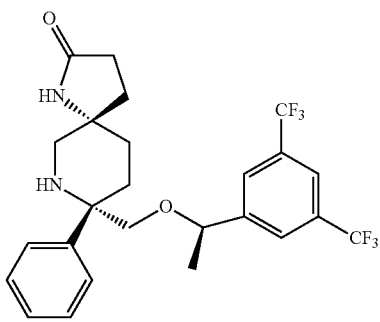 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
(b) macrogol 15-hydroxystearate in an amount of about 0.88% by weight of the total composition;
(c) at least one medium chain triglyceride in an amount of about 0.22% by weight of the total composition;
(d) refined soybean oil in an amount of about 0.12% by weight of the total composition; and
(e) a phosphate buffer, wherein the pH of the composition is about 7.5.

4. The method of claim 1, wherein the medium chain triglyceride is selected from the group consisting of caprylic acid triglyceride, capric acid triglyceride, caprylic/capric acid triglyceride, trigylceride from coconut oil, caprylic/caprylic/lauric triglyceride, caprylic/caprylic/linoleic triglyceride, caprylic/caprylic/stearic triglyceride and combinations of two or more thereof.

5. The method of claim 1, wherein the long chain triglyceride is selected from the group consisting of soybean oil, corn oil, cottonseed oil, olive oil, peanut oil, safflower oil, sesame oil, shark liver oil, ethyl oleate, castor oil, monounsaturated omega-9 fatty acid and combinations of two or more thereof.

6. The method of claim 1, wherein the macrogol 15-hydroxystearate is present in an amount of from about 0.5% to about 10.0% by weight of the total composition; the medium chain triglyceride is present in an amount of from about 0.15% to about 1.5% by weight of the total composition; and the long chain triglyceride is present in an amount of from about 0.10% to about 1.2% by weight of the total composition.

7. The method of claim 1, wherein the macrogol 15-hydroxystearate is present in an amount of from about 0.88% to about 4.84% by weight of the total composition; the medium chain triglyceride is present in an amount of from about 0.20% to about 1.20% by weight of the total composition; and the long chain triglyceride is present in an amount of from about 0.10% to about 0.75% by weight of the total composition.

8. The method of claim 1, wherein the medium chain glyceride is caprylic/capric acid triglyceride and the long chain triglyceride is refined soybean oil.

9. The method of claim 1, wherein the pharmaceutically acceptable salt is a hydrochloride salt.

10. The method of claim 1, wherein the pH of the composition is from about 7 to about 8.

11. The method of claim 10, wherein the pH of the composition is about 7.5.

12. The method of claim 1, wherein the composition further comprises a tonicity adjuster and/or a pH adjuster.

13. The method of claim 1, wherein the at least one buffer is a phosphate buffer.

14. The method of claim 13, wherein the phosphate buffer is sodium phosphate buffer.

15. The method of any of claims 1, 2, and 3, wherein the pharmaceutical composition is administered by infusion.

16. The method of any of claims 1, 2, and 3, wherein the nausea and/or vomiting are induced by chemotherapy or are post-operative nausea and/or vomiting.

17. The method of any one of claim 1, 2 or 3, wherein the compound of Formula I, or the pharmaceutically acceptable salt thereof, is present in a concentration of from 1 mg/ml to 15 mg/ml.

18. The method of claim 17, wherein the compound of Formula I, or the pharmaceutically acceptable salt thereof, is present in a concentration of from 2 mg/ml to 10 mg/ml.

19. The method of claim 18, wherein the compound of formula I or the pharmaceutically acceptable salt thereof, is present in a concentration of 2 mg/ml.

20. The method of any of claims 1, 2, and 3, wherein the pharmaceutical composition comprises the crystalline monohydrate hydrochloride salt of the compound of Formula I.

21. A method of treating acute and/or delayed nausea and/or vomiting associated with initial and repeat courses of emetogenic cancer chemotherapy comprising administration of an intravenous formulation comprising:
a) a compound of Formula I

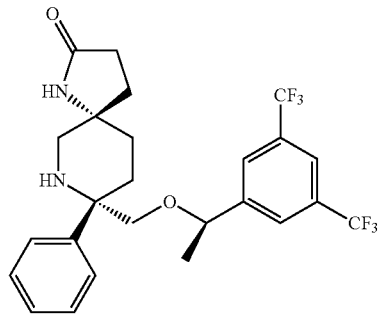 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
b) macrogol 15-hydroxystearate in an amount of from about 0.50% to about 10.0% by weight of the total composition;
c) a medium chain triglyceride in an amount of from about 0.10% to about 2.5% by weight of the total composition;
d) a long chain triglyceride in an amount of from about 0.10% to about 1.5% by weight of the total composition; and
e) at least one buffer, wherein the weight ratio of macrogol 15-hydroxystearate:medium chain triglyceride:long chain triglyceride in the composition is about 5-100:1-5:1, and wherein the pH of the composition is from about 6.5 to about 8.0; and
with incidence of hemolysis that is below 20% when administered across a population.

22. The method of any of claims 1, 2, 3, and 21, wherein the patient is a primate or a companion animal.

23. The method of claim 22, wherein the primate is a human.

24. The method of any of claims 1, 2, 3, and 21, wherein the total daily dose of the compound of Formula I or pharmaceutically acceptable salt thereof is from 1 mg/kg to 9 mg/kg patient body weight.

25. The method of claim 1 or 21 wherein the medium chain glyceride is caprylic/capric acid triglyceride.

26. The method of claim 21, wherein said intravenous formulation comprises:
(a) a compound of Formula I

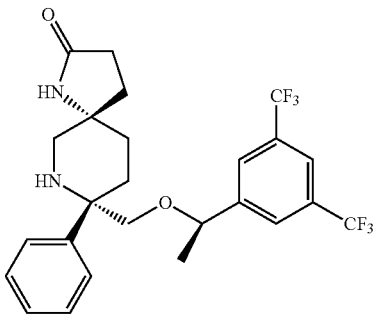 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
(b) macrogol 15-hydroxystearate in an amount of about 4.4% by weight of the total composition;
(c) at least one medium chain triglyceride in an amount of about 1.1% by weight of the total composition;
(d) refined soybean oil in an amount of about 0.66% by weight of the total composition; and
(e) a phosphate buffer, wherein the pH of the composition is about 7.5.

27. The method of claim 21, wherein said intravenous formulation comprises:
(a) a compound of Formula I

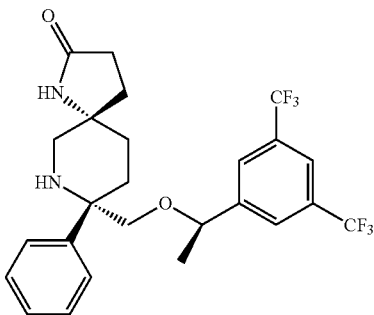 [SMILES: C[C@@H](OC[C@@]1(c2ccccc2)CC[C@]2(CCC(=O)N2)CN1)c1cc(C(F)(F)F)cc(C(F)(F)F)c1]

or a pharmaceutically acceptable salt thereof;
(b) macrogol 15-hydroxystearate in an amount of about 0.88% by weight of the total composition;
(c) at least one medium chain triglyceride in an amount of about 0.22% by weight of the total composition;
(d) refined soybean oil in an amount of about 0.12% by weight of the total composition; and
(e) a phosphate buffer, wherein the pH of the composition is about 7.5.

28. The method of claim 21, wherein the medium chain triglyceride is selected from the group consisting of caprylic acid triglyceride, capric acid triglyceride, caprylic/capric acid triglyceride, trigylceride from coconut oil, caprylic/caprylic/lauric triglyceride, caprylic/caprylic/linoleic triglyceride, caprylic/caprylic/stearic triglyceride and combinations of two or more thereof.

29. The method of claim 21, wherein the long chain triglyceride is selected from the group consisting of soybean oil, corn oil, cottonseed oil, olive oil, peanut oil, safflower oil, sesame oil, shark liver oil, ethyl oleate, castor oil, monounsaturated omega-9 fatty acid and combinations of two or more thereof.

30. The method of claim 21, wherein the macrogol 15-hydroxystearate is present in an amount of from about 0.5% to about 10.0% by weight of the total composition; the medium chain triglyceride is present in an amount of from about 0.15% to about 1.5% by weight of the total composition; and the long chain triglyceride is present in an amount of from about 0.10% to about 1.2% by weight of the total composition.

31. The method of claim 21, wherein the macrogol 15-hydroxystearate is present in an amount of from about 0.88% to about 4.84% by weight of the total composition; the medium chain triglyceride is present in an amount of from about 0.20% to about 1.20% by weight of the total composition; and the long chain triglyceride is present in an amount of from about 0.10% to about 0.75% by weight of the total composition.

32. The method of claim 21, wherein the medium chain glyceride is caprylic/capric acid triglyceride and the long chain triglyceride is refined soybean oil.

33. The method of claim 21, wherein the pharmaceutically acceptable salt is a hydrochloride salt.

34. The method of claim 21, wherein the compound of Formula I, or the pharmaceutically acceptable salt thereof, is present in a concentration of from 1 mg/ml to 15 mg/ml.

35. The method of claim 32, wherein the compound of Formula I, or the pharmaceutically acceptable salt thereof, is present in a concentration of from 2 mg/ml to 10 mg/ml.

36. The method of claim 33, wherein the compound of Formula I is present in a concentration of 2 mg/ml.

37. The method of claim 21, wherein the pH of the composition is from about 7 to about 8.

38. The method of claim 35, wherein the pH of the composition is about 7.5.

39. The method of claim 21, wherein the composition further comprises a tonicity adjuster and/or a pH adjuster.

40. The method of claim 21, wherein the at least one buffer is a phosphate buffer.

41. The method of claim 38, wherein the phosphate buffer is sodium phosphate buffer.

42. The method of claim 21, wherein the pharmaceutical composition is administered by infusion.

43. The method of any of claims 21, 26, and 27, wherein the intravenous formulation comprises the crystalline monohydrate hydrochloride salt of the compound of Formula I.

44. The method of any of claims 1, 2, 3, 21, 26, and 27 further comprising administration of at least one additional antiemetic agent.

* * * * *